United States Patent
Townsend et al.

(10) Patent No.: US 6,346,602 B1
(45) Date of Patent: Feb. 12, 2002

(54) PEPTIDE MIMICS OF THE CYTOKINE RECEPTOR COMMON γ CHAIN AND METHODS AND COMPOSITIONS FOR MAKING AND USING THE SAME

(75) Inventors: Robert Martin Townsend, Boothwyn, PA (US); Robert Korngold, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/020,065

(22) Filed: Feb. 6, 1998

Related U.S. Application Data

(60) Provisional application No. 60/036,941, filed on Feb. 7, 1997.

(51) Int. Cl.[7] .......................... A61K 38/12; C07K 5/00; C07K 7/00
(52) U.S. Cl. .......................... 530/317; 530/300; 514/9; 514/11
(58) Field of Search ................................ 530/317, 300; 530/328; 514/9, 11, 12

(56) References Cited

FOREIGN PATENT DOCUMENTS

| WO | WO 95/11312 | 4/1995 |
|---|---|---|
| WO | WO 97/28190 | 8/1997 |

OTHER PUBLICATIONS

Boussiotis et al., "Prevention of T Cell Anergy by Signaling Through the $\gamma_c$ Chain of the IL–2 Receptor", *Science*, 1994, 266, 1039–1041.

deVos et al., "Human Growth Hormone and Extracellular Domain of Its Receptor: Crystal Structure of the Complex", *Science*, 1992, 255, 306–312.

Finn, F.M. et al., in *The Proteins*, vol. II, 3rd Ed., Neurath, H. et al. (eds.), Academic Press, New York, NY, 1976, 105–253.

Gustchina, et al., "A Model of the Complex Between Interleukin–4 and Its Receptors", *Proteins: Structure, Function and Genetics*, 1995, 21, 140–148.

Kent et al., "Modern Methods for the Chemical Synthesis of Biologically Active Peptides", in *Synthetic Peptides in Biology and Medicine*, Alitalo, K. et al. (eds.), Elsevier Science Publishers, Amsterdam, 1985, 29–57.

Merrifield, "Solid Phase Peptide Synthesis. I. The Synthesis of a Tetrapeptide", *J. Am. Chem. Soc.*, 1963, 15, 2149–2154.

Miyazaki, T. et al., "Functional Activation of Jak1 and Jak3 by Selective Association with IL–2 Receptor Subunits", *Science*, 1994, 266, 1045–1047.

Noguchi, M. et al., "Interleukin–2 Receptor γ Chain Mutation Results in X–Linked Severe Combined Immunodeficiency in Humans", *Cell*, 1993, 73, 147–157.

Russell, S.M. et al., "Interaction of IL–2Rβ and $\gamma_c$ Chains with Jak1 and Jak1 and Jak3: Implications for XSCID and XCID", *Science*, 1994, 266, 1042–1044.

Townsend, R.M. et al., "Peptide Mimics of the Cytokine Receptor Common Gamma Chain", *J. Allergy Clin. Immunol.*, 1997, 99(No. 1, Part 2), p. S16, Abstract No. 67.

*Primary Examiner*—Avis M. Davenport
(74) *Attorney, Agent, or Firm*—Woodcock Washburn Kurtz Mackiewicz & Norris LLP

(57) ABSTRACT

Peptides which mimic a loop on the γ-chain that either interact with a cytokine or a γ-chain partner receptor chain of a heterodimeric cytokine receptor are disclosed. The peptides consist of 5–25 amino acids and inhibit signal transduction mediated by cytokine:receptor binding of cytokines that bind to receptors that comprise a γ-chain. Pharmaceutical compositions that comprise the peptides are disclosed. Methods of inhibiting signal transduction mediated by cytokine:receptor binding of cytokines that bind to receptors that comprise a γ-chain, methods of inhibiting cytokine mediated cell growth, proliferation, function or activity, methods of treating patients suffering from a disease disorder or condition characterized by cytokine mediated cell growth, proliferation, function or activity and methods of preventing a condition characterized by cytokine mediated cell growth, proliferation, function or activity are disclosed.

10 Claims, 16 Drawing Sheets

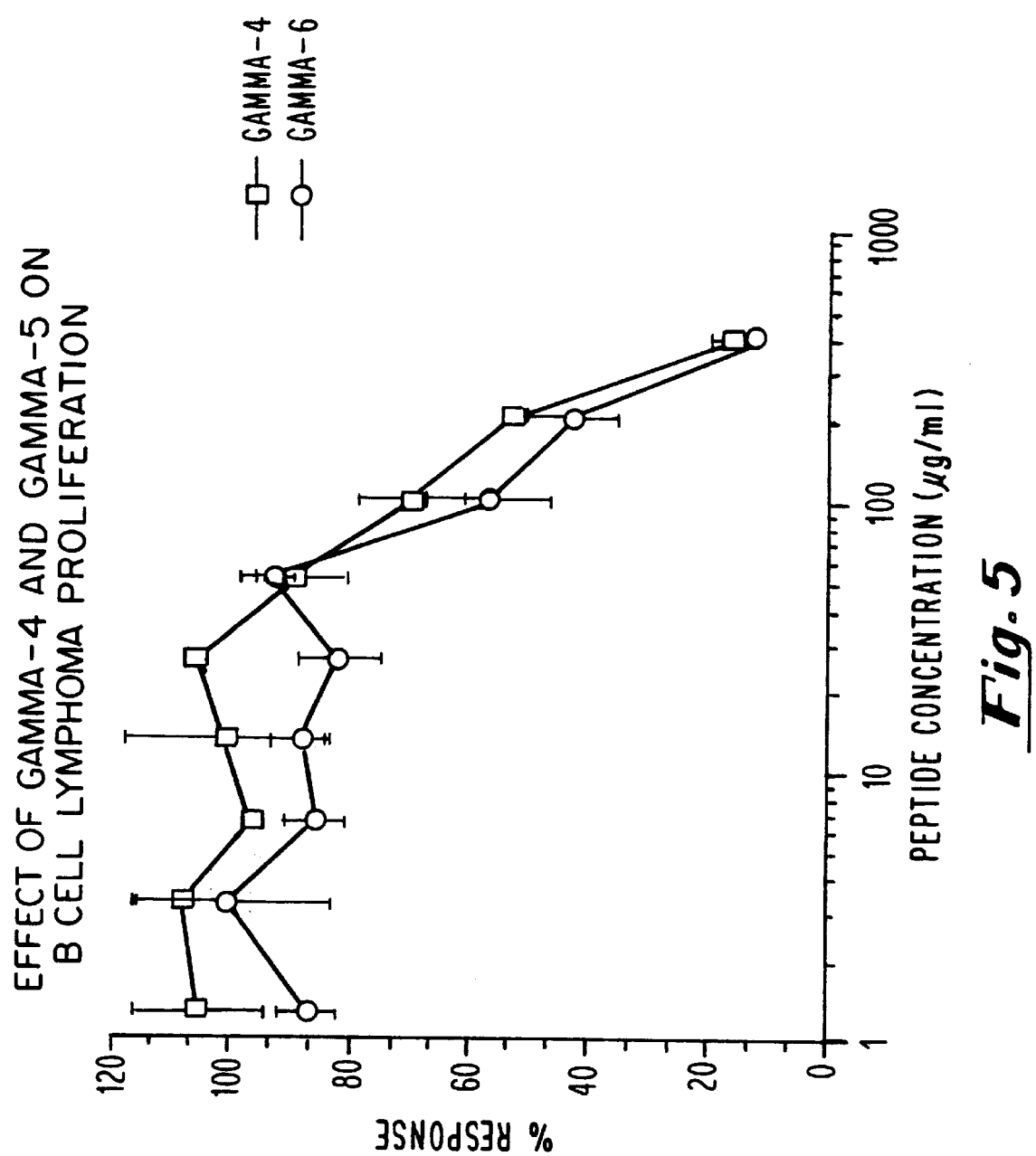

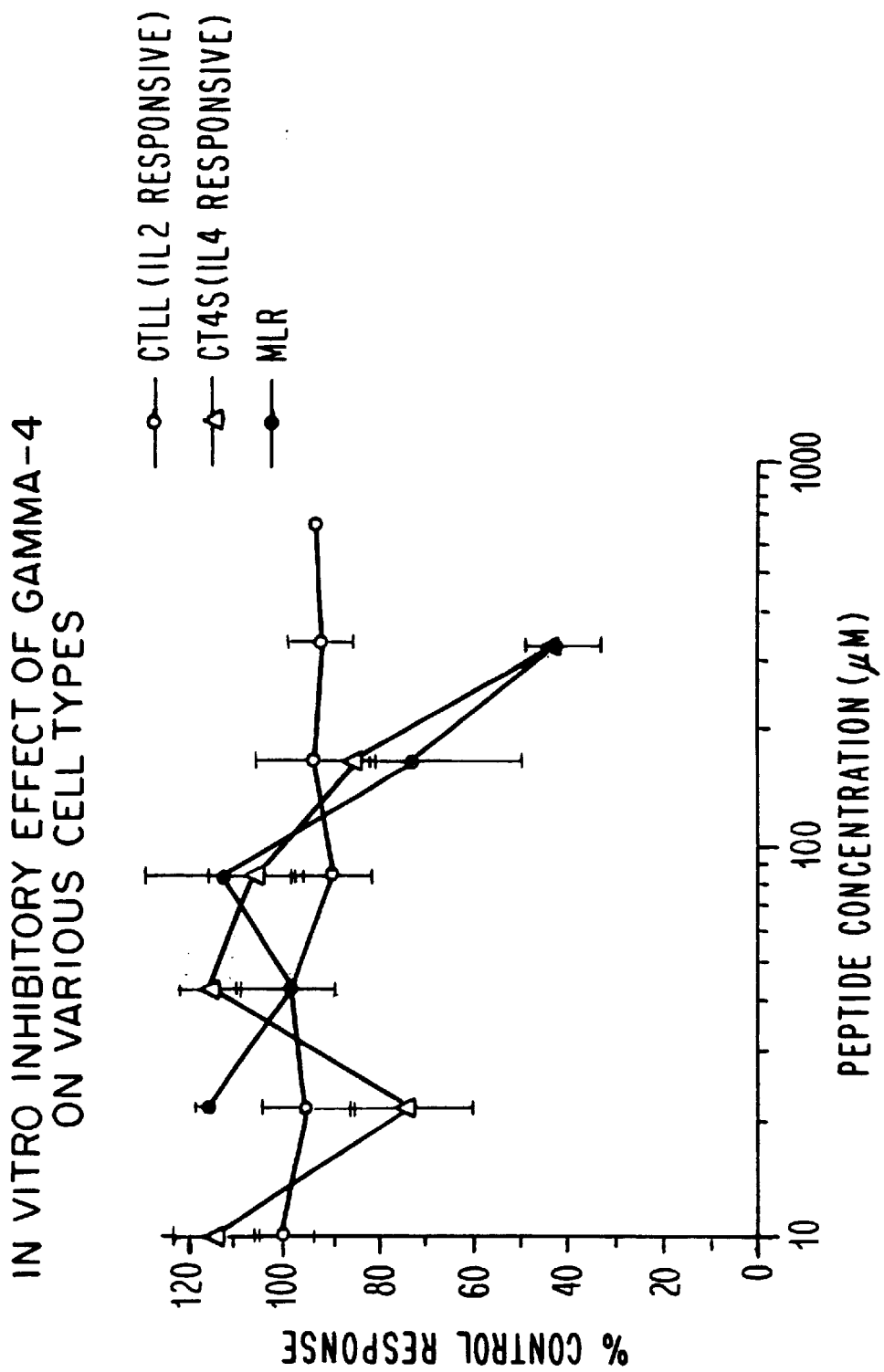

```
                       SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:1:

Ile Gln Leu Tyr Gln Thr Phe
 1               5

(2) INFORMATION FOR SEQ ID NO:2:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:2:

Ile His Leu Tyr Gln Thr Phe
 1               5

(2) INFORMATION FOR SEQ ID NO:3:

(i) SEQUENCE CHARACTERISTICS:
        (A) LENGTH: 5 amino acids
        (B) TYPE: amino acid
        (D) TOPOLOGY: both (ii) MOLECULE TYPE: peptide (xi) SEQUENCE DESCRIPTION: SEQ ID NO:3:

Cys  Gln Tyr Leu Val
 1               5

(2) INFORMATION FOR SEQ ID NO:4:
```

(i) SEQUENCE CHARACTERISTICS:
        (A) LENGTH: 6 amino acids
        (B) TYPE: amino acid
        (D) TOPOLOGY: both (ii) MOLECULE TYPE: peptide (xi) SEQUENCE DESCRIPTION: SEQ ID NO:4:

Cys Leu Glu His Leu Val
 1               5

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: both (ii) MOLECULE TYPE: peptide (xi) SEQUENCE DESCRIPTION: SEQ ID NO:5:

Cys Leu Gln Tyr Leu Thr
 1               5

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: both (ii) MOLECULE TYPE: peptide (xi) SEQUENCE DESCRIPTION: SEQ ID NO:6:

Cys Leu Glu His Leu Thr
 1               5

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:7:

Cys Leu Gln Tyr Leu Thr Gln
 1               5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:8:

Cys Leu Glu His Leu Thr Gln
 1               5

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:9:

Pro Ile Ala Gly Ser Ser Gln Gln
 1               5

(2) INFORMATION FOR SEQ ID NO:10:

(i) SEQUENCE CHARACTERISTICS:
           (A) LENGTH: 8 amino acids
           (B) TYPE: amino acid
           (D) TOPOLOGY: both (ii) MOLECULE TYPE: peptide (xi) SEQUENCE DESCRIPTION: SEQ ID NO:10:

Pro Leu Cys Gly Ser Ala Gln His
 1               5

(2) INFORMATION FOR SEQ ID NO:11:

(i) SEQUENCE CHARACTERISTICS:
           (A) LENGTH: 8 amino acids
           (B) TYPE: amino acid
           (D) TOPOLOGY: both (ii) MOLECULE TYPE: peptide (xi) SEQUENCE DESCRIPTION: SEQ ID NO:11:

Pro Leu Ala Gly Ser Ala Gln His
 1               5

(2) INFORMATION FOR SEQ ID NO:12:

(i) SEQUENCE CHARACTERISTICS:
           (A) LENGTH: 8 amino acids
           (B) TYPE: amino acid
           (D) TOPOLOGY: both (ii) MOLECULE TYPE: peptide (xi) SEQUENCE DESCRIPTION: SEQ ID NO:12:

Asn His Glu Pro Arg Phe Leu Ser
 1               5

(2) INFORMATION FOR SEQ ID NO:13:

(i) SEQUENCE CHARACTERISTICS:
           (A) LENGTH: 8 amino acids
           (B) TYPE: amino acid
           (D) TOPOLOGY: both (ii) MOLECULE TYPE: peptide (xi) SEQUENCE DESCRIPTION: SEQ ID NO:13:

Asp Tyr Arg His Lys Phe Ser Leu
 1               5

(2) INFORMATION FOR SEQ ID NO:14:

(i) SEQUENCE CHARACTERISTICS:
           (A) LENGTH: 6 amino acids
           (B) TYPE: amino acid
           (D) TOPOLOGY: both (ii) MOLECULE TYPE: peptide (xi) SEQUENCE DESCRIPTION: SEQ ID NO:14:

```
Leu Asn Leu Gln Asn Leu
  1               5

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: both (ii) MOLECULE TYPE: peptide (xi) SEQUENCE DESCRIPTION: SEQ ID NO:15:

Leu Lys Leu Gln Asn Leu
  1               5

(2) INFORMATION FOR SEQ ID NO:16:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:16:

Asn Leu Ser Glu Ser Gln Leu
  1               5

(2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:17:

Lys Leu Ser Glu Ser Gln Leu
  1               5

(2) INFORMATION FOR SEQ ID NO:18:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:18:

Cys Ile Gln Leu Tyr Gln Thr Phe Cys
  1               5

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (xi) SEQUENCE DESCRIPTION: SEQ ID NO:19:

Cys Ile His Leu Tyr Gln Thr Phe Cys
  1               5
```

(2) INFORMATION FOR SEQ ID NO:20:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (xi) SEQUENCE DESCRIPTION: SEQ ID NO:20:

Cys Leu Gln Tyr Leu Val Cys
 1            5

(2) INFORMATION FOR SEQ ID NO:21:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (xi) SEQUENCE DESCRIPTION: SEQ ID NO:21:

Cys Leu Glu His Leu Val Cys
 1            5

(2) INFORMATION FOR SEQ ID NO:22:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (xi) SEQUENCE DESCRIPTION: SEQ ID NO:22:

Cys Leu Gln Tyr Leu Thr Cys
 1            5

(2) INFORMATION FOR SEQ ID NO:23:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (xi) SEQUENCE DESCRIPTION: SEQ ID NO:23:

Cys Leu Glu His Leu Thr Cys
 1            5

(2) INFORMATION FOR SEQ ID NO:24:

(i) SEQUENCE CHARACTERISTICS:
        (A) LENGTH: 8 amino acids
        (B) TYPE: amino acid
        (D) TOPOLOGY: circular (ii) MOLECULE TYPE: peptide (xi) SEQUENCE DESCRIPTION: SEQ ID NO:24:

Cys Leu Gln Tyr Leu Thr Gln Cys
 1            5

(2) INFORMATION FOR SEQ ID NO:25:

(i) SEQUENCE CHARACTERISTICS:

(A) LENGTH: 8 amino acids
         (B) TYPE: amino acid
         (D) TOPOLOGY: circular (ii) MOLECULE TYPE: peptide (xi) SEQUENCE DESCRIPTION: SEQ ID NO:25:

Cys Leu Glu His Leu Thr Gln Cys
  1               5

(2) INFORMATION FOR SEQ ID NO:26:

(i) SEQUENCE CHARACTERISTICS:
         (A) LENGTH: 10 amino acids
         (B) TYPE: amino acid
         (D) TOPOLOGY: circular (ii) MOLECULE TYPE: peptide (xi) SEQUENCE DESCRIPTION: SEQ ID NO:26:

Cys Pro Ile Ala Gly Ser Ser Gln Gln Cys
  1               5                  10

(2) INFORMATION FOR SEQ ID NO:27:

(i) SEQUENCE CHARACTERISTICS:
         (A) LENGTH: 10 amino acids
         (B) TYPE: amino acid
         (D) TOPOLOGY: circular (ii) MOLECULE TYPE: peptide (xi) SEQUENCE DESCRIPTION: SEQ ID NO:27:

Cys Pro Leu Cys Gly Ser Ala Gln His Cys
  1               5                  10

(2) INFORMATION FOR SEQ ID NO:28:

(i) SEQUENCE CHARACTERISTICS:
         (A) LENGTH: 10 amino acids
         (B) TYPE: amino acid
         (D) TOPOLOGY: circular (ii) MOLECULE TYPE: peptide (xi) SEQUENCE DESCRIPTION: SEQ ID NO:28:

Cys Pro Leu Ala Gly Ser Ala Gln His Cys
  1               5                  10

(2) INFORMATION FOR SEQ ID NO:29:

(i) SEQUENCE CHARACTERISTICS:
         (A) LENGTH: 10 amino acids
         (B) TYPE: amino acid
         (D) TOPOLOGY: circular (ii) MOLECULE TYPE: peptide (xi) SEQUENCE DESCRIPTION: SEQ ID NO:29:

Cys Asn His Glu Pro Arg Phe Leu Ser Cys
  1               5                  10

(2) INFORMATION FOR SEQ ID NO:30:

(i) SEQUENCE CHARACTERISTICS:
         (A) LENGTH: 10 amino acids
         (B) TYPE: amino acid
         (D) TOPOLOGY: circular (ii) MOLECULE TYPE: peptide (xi) SEQUENCE DESCRIPTION: SEQ ID NO:30:

Cys Asp Tyr Arg His Lys Phe Ser Leu Cys
  1               5                  10

(2) INFORMATION FOR SEQ ID NO:31:

(i) SEQUENCE CHARACTERISTICS:
        (A) LENGTH: 8 amino acids
        (B) TYPE: amino acid
        (D) TOPOLOGY: circular (ii) MOLECULE TYPE: peptide (xi) SEQUENCE DESCRIPTION: SEQ ID NO:31:

Cys Leu Asn Leu Gln Asn Leu Cys
  1               5

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: circular (ii) MOLECULE TYPE: peptide (xi) SEQUENCE DESCRIPTION: SEQ ID NO:32:

Cys Leu Lys Leu Gln Asn Leu Cys
  1               5

(2) INFORMATION FOR SEQ ID NO:33:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (xi) SEQUENCE DESCRIPTION: SEQ ID NO:33:

Cys Asn Leu Ser Glu Ser Gln Leu Cys
  1               5

(2) INFORMATION FOR SEQ ID NO:34:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (xi) SEQUENCE DESCRIPTION: SEQ ID NO:34:

Cys Lys Leu Ser Glu Ser Gln Leu Cys
  1               5

(2) INFORMATION FOR SEQ ID NO:35:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:35:

```
Glu Arg Cys Leu Gln Tyr Leu Val Gln Tyr
  1               5                  10

(2) INFORMATION FOR SEQ ID NO:36:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:36:

Pro Ile Cys Gly Ser Ser Gln Gln
  1               5

(2) INFORMATION FOR SEQ ID NO:37:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:37:

Cys Pro Ile Cys Gly Ser Ser Gln Gln Cys
  1               5                  10
```

PEPTIDE MIMICS OF THE CYTOKINE RECEPTOR COMMON γ CHAIN AND METHODS AND COMPOSITIONS FOR MAKING AND USING THE SAME

CROSS REFERENCE TO RELATED APPLICATIONS

This application claims priority to Provisional Application No. 60/036,941 filed Feb. 7, 1997, which is incorporated herein by reference.

FIELD OF THE INVENTION

The present invention relates to molecules which have structures and functions that mimic the gamma chain that is shared by several cytokine receptors. The present invention relates to the use of such molecules to modulate cytokine activity and cytokine mediated functions.

BACKGROUND OF THE INVENTION

A family of related cytokine receptors including the receptors for IL-2, IL-4, IL-7, IL-9, IL-13 and IL-15 have been reported to share a common protein chain, the γ-chain, for maximal ligand induced receptor binding and signaling. The γ-chain is a member of the cytokine receptor superfamily which includes receptors for growth hormone, erythropoietin, IL-3, IL-2, IL-4, IL-7, IL-6 and GM-CSF. The γ-chain is a 64 kd protein with a fibronectin type II and CKR-SF domain which share structural homology.

The crystal structure of the human growth hormone receptor has been published by deVos A. M., et al. 1992 *Science* 255:306–312, which is incorporated herein by reference, and shows that the receptors form a homodimer to bind ligand and induce a signal. The receptors for IL-4 have been shown to be in the form of a heterodimer consisting of IL-4α and the common γ-chain. A model for the human IL-4:IL-4-Receptor interaction has been published by Gustchina, A. et al. 1995 PROTEINS: *Structure, Function and Genetics* 21:140–148, which is incorporated herein by reference.

Cytokine:receptor complexes are very important mediators of many immune responses. For example, T cell growth and differentiation is regulated in part by IL-2, IL-4, IL-7, IL-9, and IL-15. These cytokines have also been reported to play a role in other immunological functions as well.

Without the γ-chain, the cytokine receptors which normally form complexes with the γ-chain are much less efficient in binding their ligands and thus transmitting their signals to the target cells. Evidence for the central role of the γ-chain includes the findings that mutations in this receptor have been demonstrated to be the causative factor in the development of severe combined immunodeficiency. Recently, Boussiotis, V. A. et al. 1994 *Science* 266:1039–1047, which is incorporated herein by reference, demonstrated that the development of T cell anergy can be abrogated by signaling through this receptor by various means.

The function and activity of cells of the immune system are regulated and directed by cytokine:receptor interactions as is signaling which induces growth and proliferation. The activation of T cells and B cells is regulated by cytokine:receptor interactions including cytokine:receptor interactions involving receptors which include the γ-chain in a heterodimer.

There is a need for pharmaceutical compositions which can effectively inhibit the immune responses mediated by cytokine:receptor interactions. There is a need for a method of inhibiting cytokine mediated cell activation, function, growth and/or proliferation. There is a need for pharmaceutical compositions which can effectively inhibit signaling that involves receptors which include the γ-chain. There is a need for compositions and methods which can inhibit or suppress immune responses in order to therapeutically or prophylactically treat individuals who have conditions, diseases or disorders involving immune abnormal or undesirable immunological activity.

SUMMARY OF THE INVENTION

The present invention relates to peptide mimics of the loops on the γ-chain which either interact with cytokines or the partners of the γ-chain in heterodimeric cytokine receptors that include the γ-chain. The peptides of the present invention are based on human and murine γ-chain sequences. The sequences homology for the human and murine γ-chain is high (71% identical and 82% similar) making the translation from one species to the next more direct.

The peptide mimics bind to the cytokine or partner receptor and inhibit cytokine activity. Inhibitors of the common γ-chain inhibit the function of IL-2, IL-4, IL-7, IL-9, IL-13 and IL-15 by preventing their binding to their respective receptors. Thus, the inhibition of these cytokine mediated events leads to immuno-suppressive responses which are beneficial for the prevention or treatment of numerous auto-immune diseases and graft rejection following various types of transplant procedures as well as diseases associated with hyperproliferation of T cells and/or B cells. For example, many lymphomas are dependent on some of these cytokines (IL-2 for T cell lymphomas and IL-4 for B cell lymphomas) for growth.

The present invention relates to peptides that consist of 5 to 25 amino acids including: SEQ ID NO:1 IQLYQTF, SEQ ID NO:2 IHLYQTF, SEQ ID NO:3 CLQYLV, SEQ ID NO:4 CLEHLV, SEQ ID NO:5 CLQYLT, SEQ ID NO:6 CLEHLT, SEQ ID NO:7 CLQYLTQ, SEQ ID NO:8 CLEHLTQ, SEQ ID NO:9 PIAGSSQQ, SEQ ID NO:36 PICGSSQQ, SEQ ID NO:10 PLCGSAQH, SEQ ID NO:11 PLAGSAQH, SEQ ID NO:12 NHEPRFLS, SEQ ID NO:13 DYRHKFSL, SEQ ID NO:14 LNLQNL, SEQ ID NO:15 LKLQNL, SEQ ID NO:16 NLSESQL, SEQ ID NO:17 KLSEQL or such an amino acid sequence with one or more conservative substitutions, wherein the peptide inhibits cytokine mediated signal transduction.

The peptides of the invention preferably have constrained conformations and most preferably are cyclic. In preferred embodiments, cysteine residues are provided at the termini of the peptides to form di-sulfide bonds which result in the formation of cyclic peptides.

According to some embodiments of the present invention, peptides are selected from the group consisting of: SEQ ID NO:18 CIQLYQTFC, SEQ ID NO:19 CIHLYQTFC, SEQ ID NO:20 CLQYLVC, SEQ ID NO:21 CLEHLVC, SEQ ID NO:22 CLQYLTC, SEQ ID NO:23 CLEHLTC, SEQ ID NO:24 CLQYLTQC, SEQ ID NO:25 CLEHLTQC, SEQ ID NO:26 CPIAGSSQQC, SEQ ID NO:37 CPICGSSQQC, SEQ ID NO:27 CPLCGSAQHC, SEQ ID NO:28 CPLAGSAQHC, SEQ ID NO:29 CNHEPRFLSC, SEQ ID NO:30 CDYRHKFSLC, SEQ ID NO:31 CLNLQNLC, SEQ ID NO:32 CLKLQNLC, SEQ ID NO:33 CNLSESQLC, SEQ ID NO:34 CKLSESQLC and derivative peptides thereof. The derivative peptides consist of amino acid sequences which contain one or more conservative substitutions. Conservative substitutions include the following:

I may be substituted with V, A or L;
Q may be substituted with N;
L may be substituted with V, A or I;
Y may be substituted with F;
V may be substituted with I, A or L;
S may be substituted with T;
A may be substituted with V, I or L;
N may be substituted with Q;
E may be substituted with D;
F may be substituted with Y;
D may be substituted with E; and
I may be substituted with V, A or L.

In some preferred embodiments, the V in sequences SEQ ID NO:3 CLQYLV and SEQ ID NO:4 CLEHLV are substituted with T to improve solubility in aqueous solutions. Accordingly, peptides SEQ ID NO:22 CLQYLTC, SEQ ID NO:23 CLEHLTC, SEQ ID NO:24 CLQYLTQC and SEQ ID NO:25 CLEHLTQC are provided.

The peptides of the invention are derived from sequences of the murine or human cytokine receptor common gamma chain.

The peptides correspond to murine cytokine receptor gamma common chain residues SEQ ID NO:1 IQLYQTF (100–106), SEQ ID NO:3 CLQYLV (161–166), PICGSSQQ (207–214), SEQ ID NO:12 NHEPRFLS (181–188), SEQ ID NO:14 LNLQNL (124–129), SEQ ID NO:16 NLSESQL (142–148) and the corresponding sequences from the human cytokine receptor gamma common chain, i.e. SEQ ID NO: 2 IHLYQTF, SEQ ID NO:4 CLEHLV, SEQ ID NO:11 PLAGSAQH, SEQ ID NO:13 DYRHKFSL, SEQ ID NO:15 LKLQNL and SEQ ID NO:17 KLSEQL.

The peptides SEQ ID NO:18 CIQLYQTFC, SEQ ID NO:19 CIHLYQTFC, SEQ ID NO:20 CLQYLVC, SEQ ID NO:21 CLEHLVC, SEQ ID NO:26 CPIAGSSQQC, SEQ ID NO:37 CPICGSSQQC, SEQ ID NO:27 CPLCGSAQHC, SEQ ID NO:28 CPLAGSAQHC, SEQ ID NO:29 CNHEPRFLSC, SEQ ID NO:30 CDYRHKFSLC, SEQ ID NO:31 CLNLQNLC and SEQ ID NO:32 CLKLQNLC are modeled to mimic the regions of the cytokine receptor gamma common chain predicted to interact with ligands and the peptides SEQ ID NO:33 CNLSESQLC and SEQ ID NO:34 CKLSESQLC are modeled to mimic the regions of the cytokine receptor gamma common chain predicted to interact with other cytokine receptor chains with which the gamma chain forms heterodimers as an active receptor complex.

According to the invention, the peptides of the invention inhibit cytokine mediated signaling that involves cytokine receptors which include the gamma chain. Cytokines IL-2, IL-4, IL-7, IL-9, IL-13 and IL-15 each interact with receptor complexes that include the gamma chain. Accordingly, the peptides of the invention can be used to inhibit IL-2, IL-4; IL-7, IL-9, IL-13 and IL-15 signaling. Through this inhibition, the peptides of the invention are useful to suppress immunological responses and functions. For example, these cytokines are involved in immunological activity in which cells are induced to grow, proliferate and/or release factors, cytokines or other molecules including antibodies. The peptides of the invention can be used to inhibit these activities.

Inhibition of T cell and/or B cell proliferation is useful in the treatment of many diseases and conditions including, but not limited to, leukemia, lymphoma, graft versus host disease and other transplant rejections, allergies, asthma and autoimmune and inflammatory diseases such as rheumatoid arthritis, lupus, multiple sclerosis and myasthenia gravis. The peptides of the invention can also inhibit the growth of B cells and T cells and/or inhibit T cells and B cells from releasing substances. Thus, by inhibiting cell growth and/or proliferation and/or function of cells involved in the immune system, the peptides can be useful to suppress the immune system.

The present invention relates to methods of preventing and treating diseases involving or mediated by cells of the immune system. According to some embodiments of the invention, patients are administered compounds of the invention in an amount sufficient to suppress immune function sufficiently to have a therapeutic effect on patients suffering from such diseases involving undesirable function, activity, growth or proliferation of cells of the immune system. According to some embodiments of the invention, patients are administered compounds of the invention in an amount sufficient to suppress immune function sufficiently to have a preventive effect on patients at risk of developing diseases, disorders or conditions involving undesirable function, activity, growth or proliferation of cells of the immune system.

BRIEF DESCRIPTION OF THE FIGURES

FIG. 5 shows data from experiments described in Example 1 testing the ability of peptides of the invention as described in Example 1 to inhibit CH12.CX proliferation.

FIGS. 6A–6F shows data from experiments described in Example 2 testing the ability of peptides of the invention as described in Example 1 to inhibit cytokine mediated activity of various cell lines.

DETAILED DESCRIPTION OF THE INVENTION

Figure 1A:
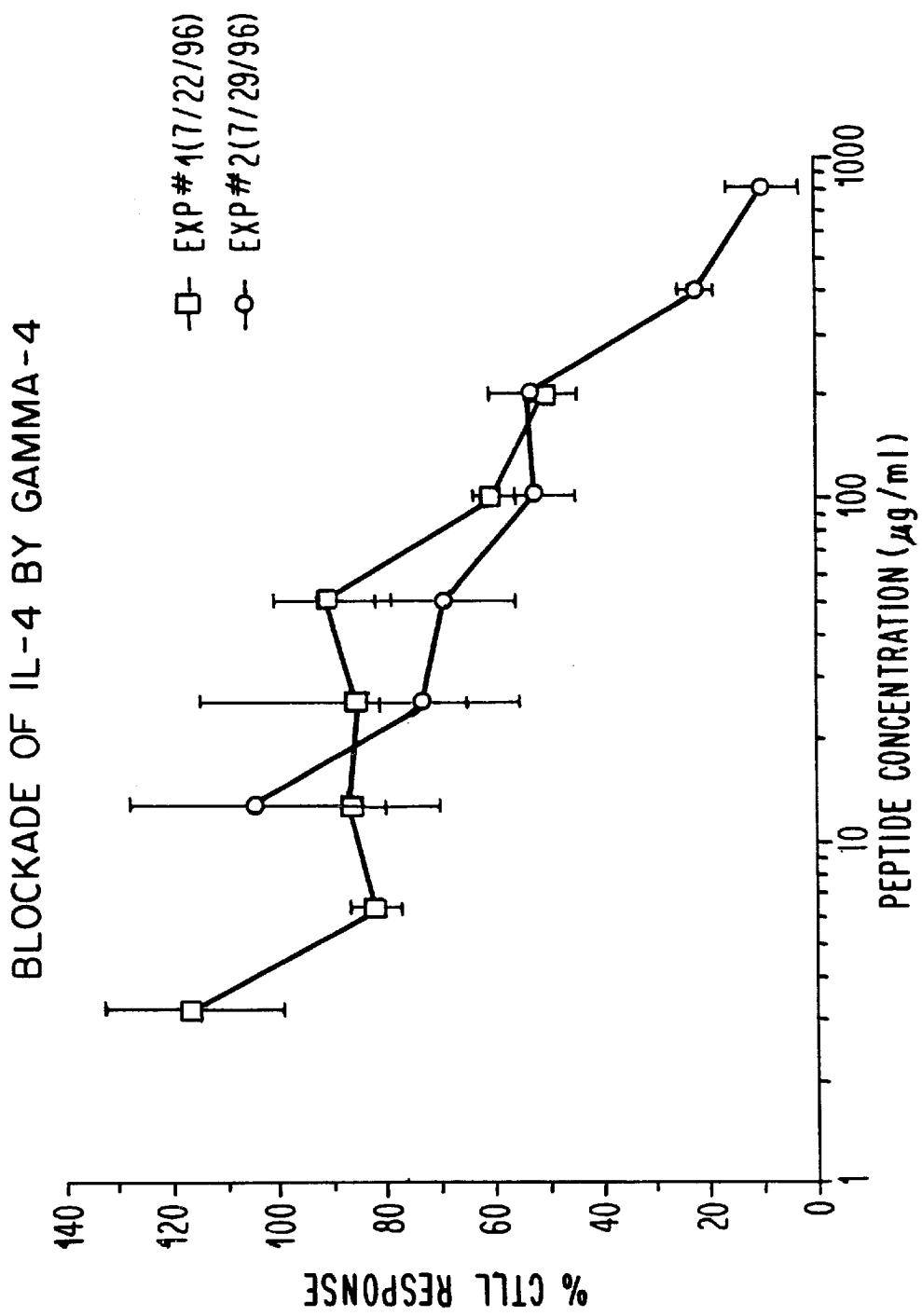
FIGS. 1A–1D shows data from experiments described in Example 1 testing peptides gamma-4 and gamma-5 of the invention as described in Example 1 to determine their effect on the response of cells to exogenous cytokine IL-2 or IL-4. The cell line used proliferates in the absence of peptide. The data shows that the addition of peptide inhibits cell proliferation in response to addition of the IL-4 and that such inhibition is dose dependent.
Figure 1B:
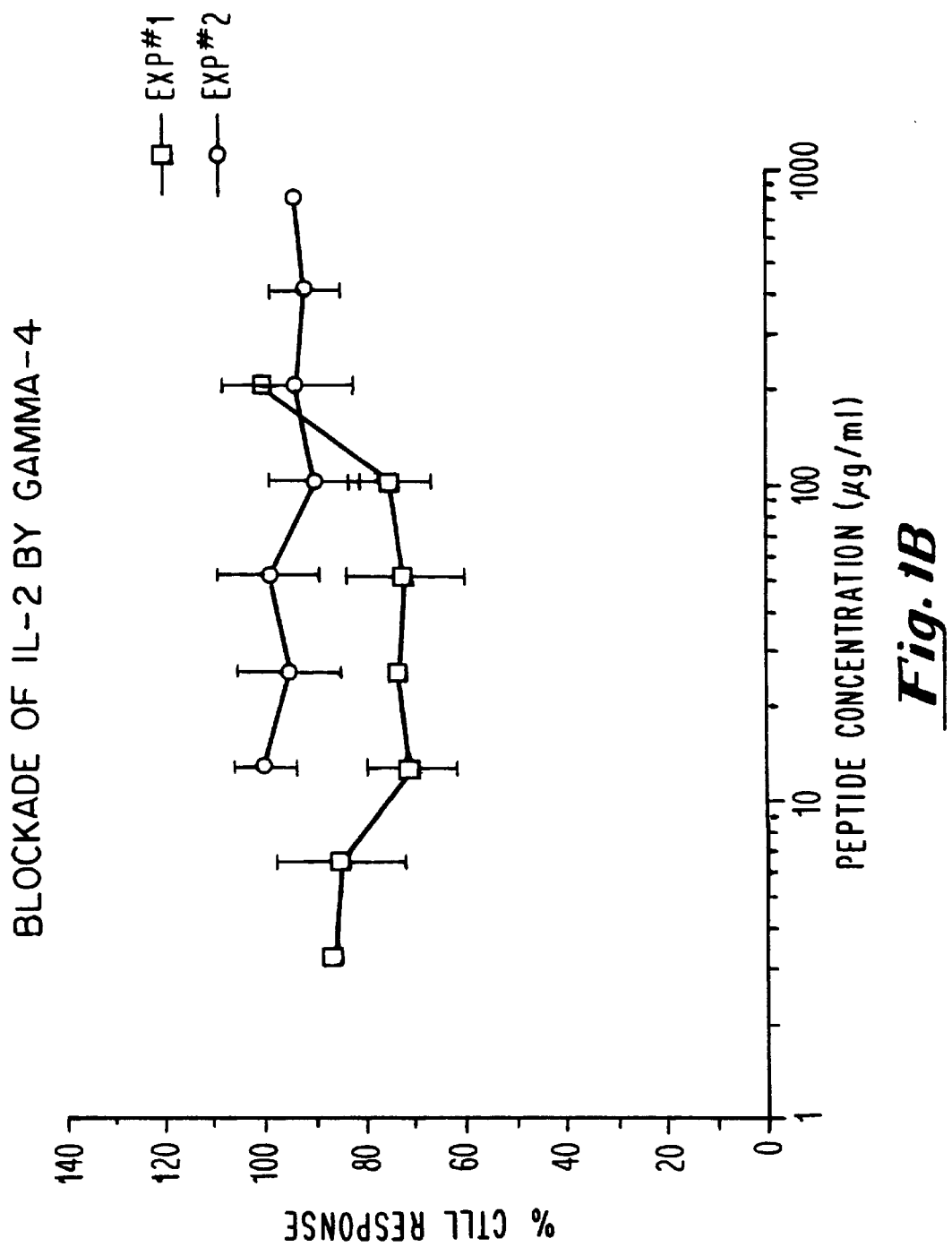
Figure 1C:
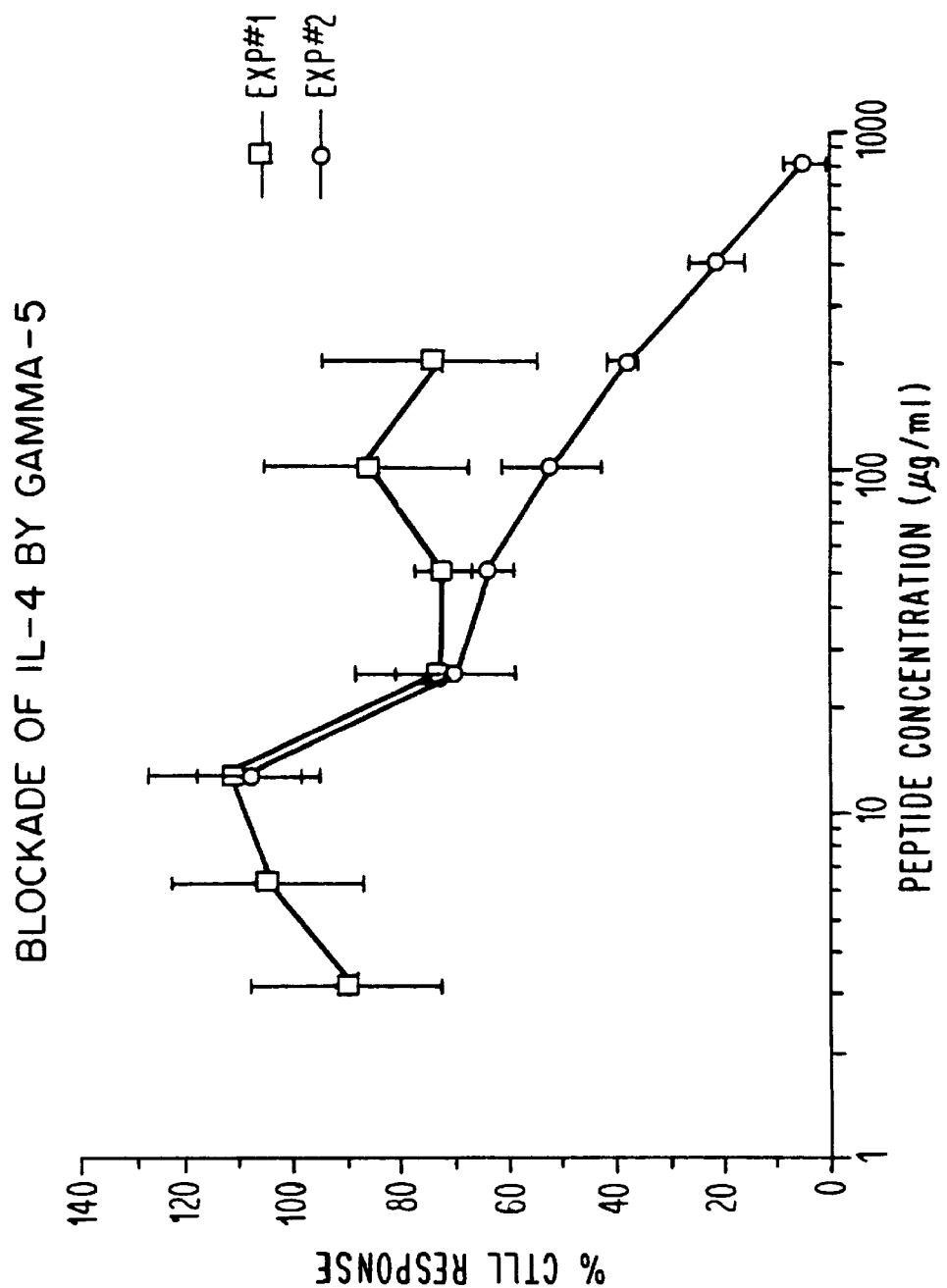
Figure 1D:
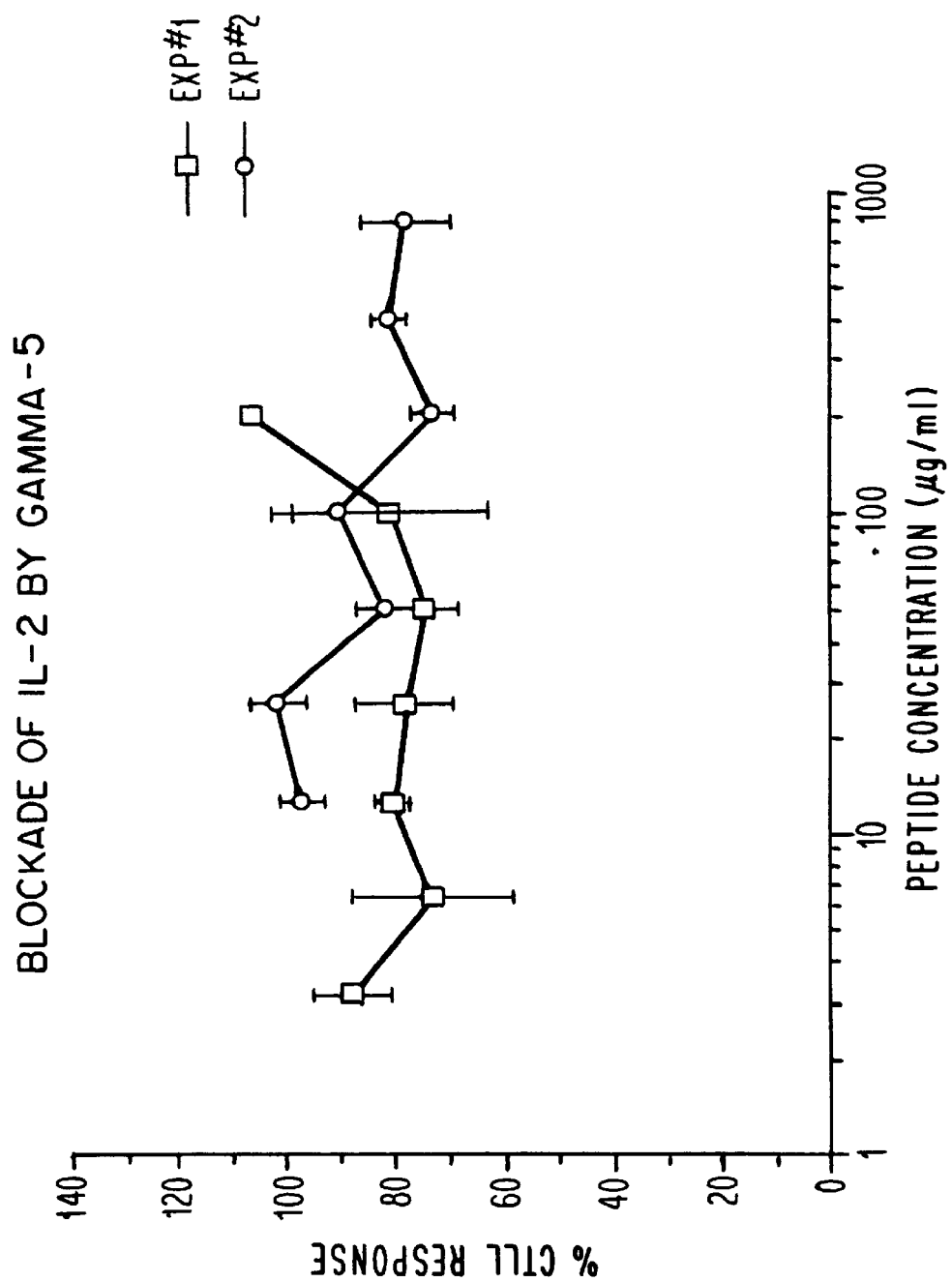
Figure 2:
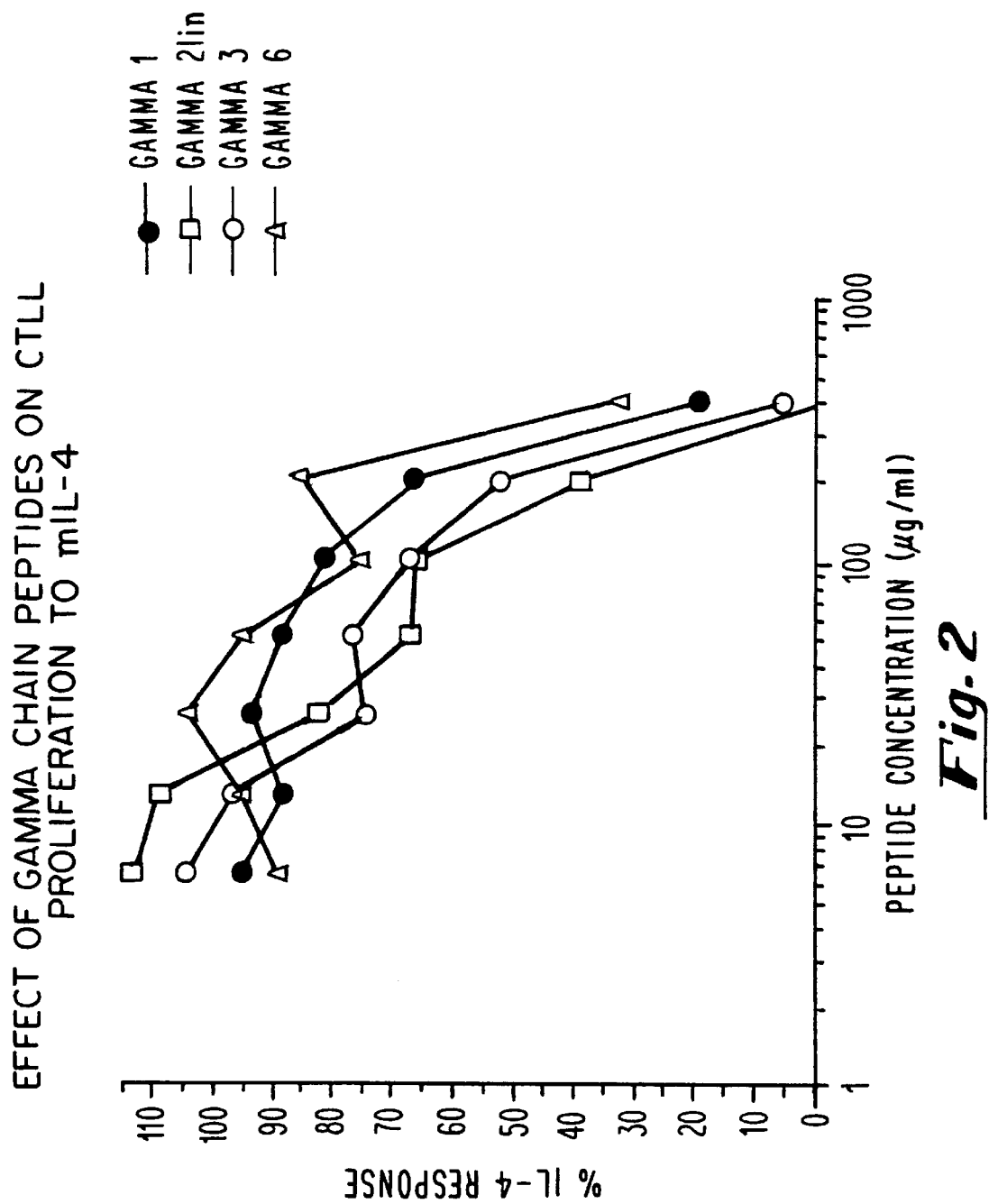
FIG. 2 shows data from experiments described in Example 1 testing peptides of the invention as described in Example 1 to determine their effect on the response of cells to exogenous murine IL-4. The cell line used proliferates in the absence of peptide. The data shows that the addition of peptide inhibits cell proliferation in response to addition of mIL-4 and that such inhibition is dose dependent.
Figure 3:
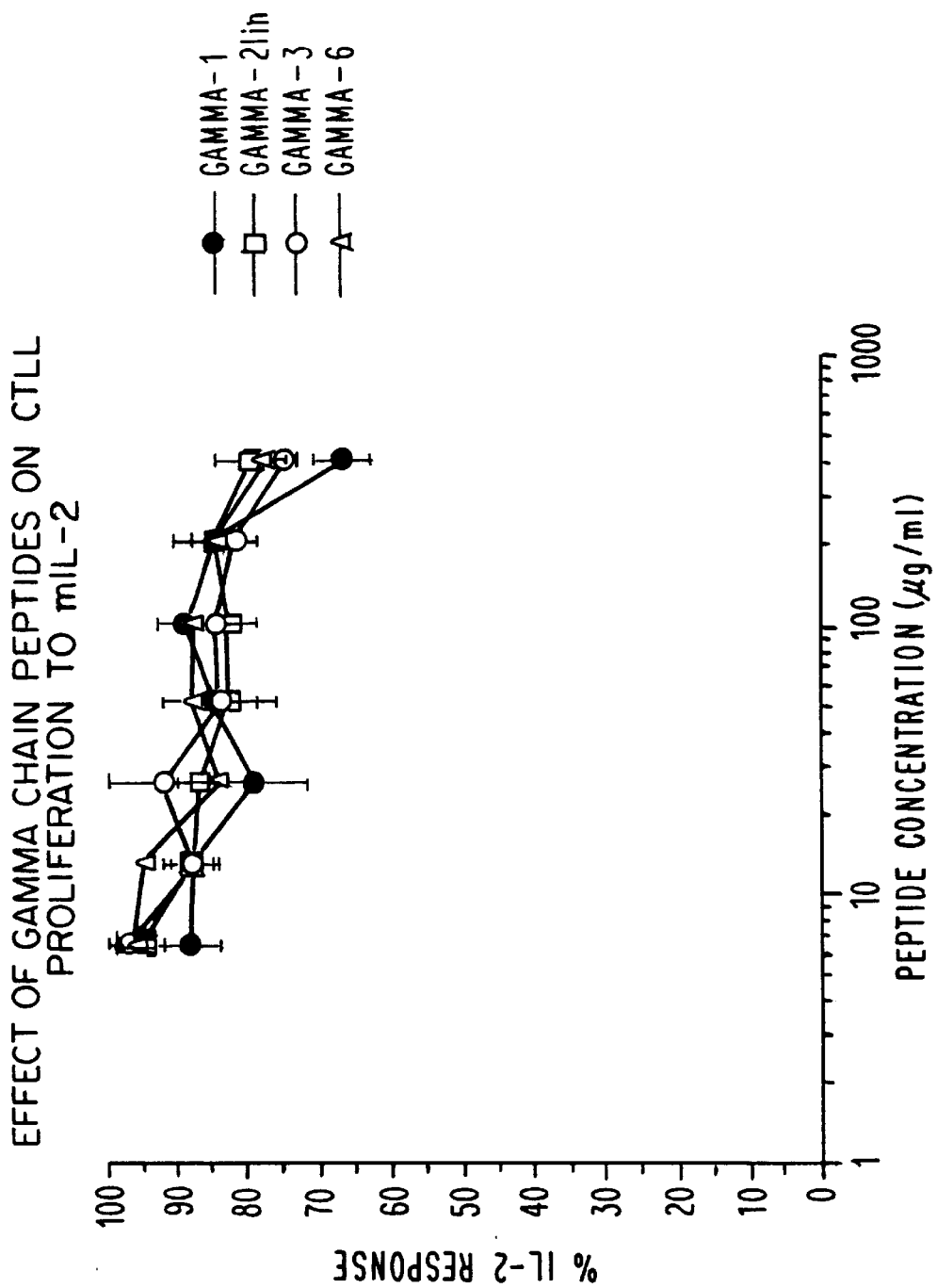
FIG. 3 shows data from experiments described in Example 1 testing peptides of the invention as described in Example 1 to determine their effect on the response of cells to exogenous murine IL-2. The cell line used proliferates in the absence of peptide.

The present invention relates to molecules that have a molecular surface similar to a molecular surface of cytokine receptor common gamma chain. The peptides of the invention interact with molecules which ordinarily interact with the gamma chain and result in signal transduction. Not wishing to bound by any theory, it appears that the peptides of the invention thereby inhibit signal transduction by inhibiting cytokine:receptor binding either by binding to the cytokine or by binding to a cytokine receptor chain which forms heterodimers with the gamma chain in order to form a functional receptor complex.

According to some embodiments of the present invention, the invention can be represented by the formula:

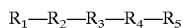

wherein:

$R_1$, $R_2$, $R_3$, $R_4$ and $R_5$ taken together are 5–25 amino acids or less and $R_1$ is a linking moiety, preferably cysteine or penicillamine;

$R_2$ is 0–10 amino acids, preferably 0 amino acids;

$R_3$ is SEQ ID NO:1 IQLYQTF, SEQ ID NO: 2 IHLYQTF, SEQ ID NO:3 CLQYLV, SEQ ID NO:4 CLEHLV, SEQ ID NO:5 CLQYLT, SEQ ID NO:6 CLEHLT, SEQ ID NO:7 CLQYLTQ, SEQ ID NO:8 CLEHLTQ, SEQ ID NO:9 PIAGSSQQ, SEQ ID NO:10 PLCGSAQH, SEQ ID NO:11 PLAGSAQH, SEQ ID NO:12 NHEPRFLS, SEQ ID NO:13 DYRHKFSL, SEQ ID NO:14 LNLQNL, SEQ ID NO:15 LKLQNL, SEQ ID NO:16 NLSESQL, SEQ ID NO:17 KLSEQL or such an amino acid sequence with one or more conservative substitutions;

$R_4$ is 0–10 amino acids, preferably 0 amino acids; and $R_5$ is a linking moiety, preferably cysteine or penicillamine.

It is preferred that $R_1$ is cysteine or penicillamine. It is more preferred that $R_1$ is cysteine.

It is preferred that $R_2$ is 0 amino acids.

It is preferred that $R_3$ is SEQ ID NO:1 IQLYQTF, SEQ ID NO: 2 IHLYQTF, SEQ ID NO:3 CLQYLV, SEQ ID NO:4 CLEHLV, SEQ ID NO:5 CLQYLT, SEQ ID NO:6 CLEHLT, SEQ ID NO:7 CLQYLTQ, SEQ ID NO:8 CLEHLTQ, SEQ ID NO:9 PIAGSSQQ, SEQ ID NO:10 PLCGSAQH, SEQ ID NO:11 PLAGSAQH, SEQ ID NO:12 NHEPRFLS, SEQ ID NO:13 DYRHKFSL, SEQ ID NO:14 LNLQNL, SEQ ID NO:15 LKLQNL, SEQ ID NO:16 NLSESQL or SEQ ID NO:17 KLSEQL.

It is preferred that conservative substititions include I, V, A and L are interchangeable, Q and N are interchangeable, Y and F are interchangeable, S and T are interchangeable and E and D are interchangeable.

It is preferred that $R_4$ is 0–1 amino acids. It is preferred that $R_4$ is 0 amino acids.

It is preferred that $R_5$ is cysteine or penicillamine. It is more preferred that $R_5$ is cysteine.

In preferred embodiments, the compound is SEQ ID NO:18 CIQLYQTFC, SEQ ID NO:19 CIHLYQTFC, SEQ ID NO:20 CLQYLVC, SEQ ID NO:21 CLEHLVC, SEQ ID NO:22 CLQYLTC, SEQ ID NO:23 CLEHLTC, SEQ ID NO:24 CLQYLTQC, SEQ ID NO:25 CLEHLTQC, SEQ ID NO:26 CPIAGSSQQC, SEQ ID NO:27 CPLCGSAQHC, SEQ ID NO:28 CPLAGSAQHC, SEQ ID NO:29 CNHEPRFLSC, SEQ ID NO:30 CDYRHKFSLC, SEQ ID NO:31 CLNLQNLC, SEQ ID NO:32 CLKLQNLC, SEQ ID NO:33 CNLSESQLC or SEQ ID NO:34 CKLSESQLC.

The present invention provides synthetic peptides that are 5–25 amino acids and comprise amino acid sequences from human or murine cytokine receptor gamma common chain. Non-gamma chain amino acid sequences are provided in some embodiments. The peptides are conformationally restricted, and are generally cyclized. In some embodiments, non-gamma chain sequences are included for the purposes of conformational restriction. In embodiments that comprise both gamma chain and non-gamma chain sequences, at least 20–25% of the amino acid sequence of the peptides of the present invention are derived from he gamma chain. It is preferred that greater than about 20–25% of the amino acid sequence of the peptides of the present invention are derived from the gamma chain, more preferably 30–40% and more preferably greater than 50%. In some embodiments, the percentage of amino acid sequence of the peptides of the present invention derived from gamma chain is about 60% or about 75% or more.

The peptides of the present invention may be prepared by any of the following known techniques. Conveniently, the peptides may be prepared using the solid-phase synthetic technique initially described in Merrifield (1963) *J. Am. Chem. Soc.* 15:2149–2154. Other peptide synthesis techniques may be found, for example, in M. Bodanszky et al., *Peptide Synthesis,* John Wiley & Sons, 2d Ed. (1976); Kent and Clark-Lewis in *Synthetic Peptides in Biology and Medicine,* p. 295–358, eds. Alitalo, K., Partanen, P. and Vakeri, A., Elsevier Science Publishers, (Amsterdam, 1985); as well as other reference works known to those skilled in the art. A summary of peptide synthesis techniques may be found in J. Stuart and J. D. Young, *Solid Phase Peptide Synthelia,* Pierce Chemical Company, Rockford, Ill. (1984). The synthesis of peptides by solution methods may also be used, as described in *The Proteins,* Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry,* Plenum Press, New York, N.Y. (1973).

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

The present peptides may also be prepared by recombinant DNA techniques, although such methods are not preferred because of the need for purification and subsequent chemical modifications to conformationally restrain the peptides.

In addition to peptides which comprise L amino acids, pharmaceutical compositions according to the present invention may comprise peptides made up of D amino acids. Because most enzymes involved in degradation recognize a tetrahedral alpha-carbon, the D-amino acids were utilized in order to avoid enzyme recognition and subsequent cleavage. Our computer studies indicate that the same folded presentation of the peptide is accomplished by reversing the amino acid sequence, employing D-amino acids. Thus, peptides comprised of D amino acids are less susceptible to degradation.

Conservative substitutions in the amino acid sequence may be made. Those having ordinary skill in the art can readily design compounds of the invention with conservative substitutions for CD8 amino acids. For example, following what are referred to as Dayhof's rules for amino acid substitution (Dayhof, M. D. (1978) *Nat. Biomed. Res. Found.,* Washington, D.C. Vol. 5, supp. 3), amino acid residues in a peptide sequence may be substituted with comparable amino acid residues. Such substitutions are well known and are based the upon charge and structural characteristics of each amino acid.

Synthesized peptides may be circularized in order to mimic the geometry of those portions as they occur in the gamma chain. Circularization may be facilitated by disulfide bridges between cysteine residues. Alternatively, the peptides may be circularized by means of covalent bonds, such as amide bonds, between amino acid residues of the peptide such as those at or near the amino and carboxy termini.

Peptides for use in pharmaceutical compositions of the present invention may be designed following the guidelines set out herein and using well known processes. Methods of synthesizing peptides and circularizing them may be performed routinely using standard techniques and readily available starting materials.

The present invention relates to methods of therapeutically or prophylactically treating an individual suffering from or susceptible to a disease, condition or disorder associated with T cell or B cell growth, proliferation and/or secretion of biologically active material. The present invention relates to methods of therapeutically or prophylactically treating an individual suffering from or susceptible to a disease, condition or disorder by suppressing immunological responses through the inhibition of cytokine mediated signal transduction.

Examples of diseases condition and disorders for which the present invention may be employed include T cell and B cell leukemias and lymphomas, inflammatory and autoimmune diseases, allergies and conditions and rejections associated with transplantation protocols.

Those having ordinary skill in the art can readily identify individuals suspected of suffering from or being susceptible to conditions, diseases and disorders which can be effectively treated or prevented by inhibition of cytokine mediated immune responses effected by the peptides of the invention. Those with ordinary skill in the art could readily identify individuals for whom administration of the compounds of the invention would be beneficial to alleviate or prevent immune responses. Treatment may be provided prophylactically or in response to symptoms associated with undesirable immune responses or activity of cells of the immune system. Pharmaceutical compositions useful in the methods of the present invention comprise the compounds described herein.

The method of therapeutically or prophylactically treating an individual comprises administering to such an individual an effective amount of a peptide according to the invention. A prophylactically effective amount is an amount which is effective to prevent or decrease the immune response associated with disease condition or disorder to be prevented. A therapeutically effective amount is an amount which is effective to decrease or eliminate symptoms in an individual suffering from such diseases, conditions and disorders rejection. Those having ordinary skill in the art can readily and routinely determine the ranges of both prophylactically and therapeutically effective amounts of the peptides of the invention without undue experimentation.

The present invention provides pharmaceutical compositions that comprise the peptides of the invention and pharmaceutically acceptable carriers or diluents. The pharmaceutical composition of the present invention may be formulated by one having ordinary skill in the art. Suitable pharmaceutical carriers are described in Remington's Pharmaceutical Sciences, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. In some embodiments, compounds are administered 1–2 days prior to transplantation, preferably 4–12 hours. Compounds may be delivered during transplantation procedures. In some embodiments, compounds are administered for 2 weeks to 2 months after transplantation procedures.

The pharmaceutical compositions of the present invention may be administered by any means that enables the active agent to reach the targeted cells. These methods include, but are not limited to, oral, topical, intradermal, subcutaneous, intravenous, intramuscular and intraparenteral modes of administration. The compounds may be administered singly or in combination with other compounds. The compounds of the invention are preferably administered with a pharmaceutically acceptable carrier selected on the basis of the selected route of administration and standard pharmaceutical practice.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

EXAMPLES

Example 1

Novel peptide mimics that were derived from the sequence of the cytokine receptor common gamma chain were designed for the purpose of inhibiting cytokine receptor signal transduction. Such peptides are capable of inhibiting the functions of many immune cells which are responsive to these cytokines and thus are useful in the treatment of various maladies such as leukemia, lymphoma, inflammatory diseases, autoimmune disease, transplant rejection, allergies and others.

Based on the structural data, 5 sequences (γ1–5) were identified that are predicted to interact with the ligands of the γ-chain and one sequence (γ6) that is predicted to interact with the heterodimeric partner receptors was synthesized. The sequences are as follows:

|  | Murine | Human | % Identity |
|---|---|---|---|
| γ1 ($I_{100}$->$F_{106}$) | SEQ ID NO:1 IQLYQTF | SEQ ID NO:2 IHLYQTF | 86 |
| γ2 ($C_{161}$->$V_{166}$) | SEQ ID NO:3 CLQYLV | SEQ ID NO:4 CLEHLV | 67 |
| γ3 ($P_{207}$->$Q_{214}$) | SEQ ID NO:36 PICGSSQQ | SEQ ID NO:10 PLCGSAQH | 63 |
| γ4 ($N_{181}$->$L_{188}$) | SEQ ID NO:12 NHEPRFLS | SEQ ID NO:13 DYRHKFSL | 50 |
| γ5 ($L_{124}$->$L_{129}$) [001b] | SEQ ID NO:14 LNLQNL | SEQ ID NO:15 LKLQNL | 83 |
| γ6 ($N_{142}$->$L_{148}$) | SEQ ID NO:16 NLSESQL | SEQ ID NO:17 KLSEQL | 86 |

Peptides have been synthesized based on these sequences and cyclized by the addition of cysteine residues at either end and disulfide bridging. We have tested the following murine peptides in vitro for their ability to inhibit cytokine driven proliferation of cell lines such as CTLL (T-cell) and CH12.CX (B-cell) as well as in MLRs:

| Peptide | Sequence |
|---|---|
| γ1 ($I_{100}$->$F_{106}$) | SEQ ID NO:18 CIQLYQTFC |
| γ2 ($C_{161}$->$V_{166}$) | SEQ ID NO:20 CLQYLVC |
| γ3 ($P_{207}$->$Q_{214}$) | SEQ ID NO:26 CPIAGSSQQC |
| γ4 ($N_{181}$->$L_{188}$) | SEQ ID NO:29 CNHEPRFLSC |
| γ5 ($L_{124}$->$L_{129}$) | SEQ ID NO:31 CLNLQNLC |
| γ6 ($N_{142}$->$L_{148}$) | SEQ ID NO:33 CNLSESQLC |
| γ2 lin. | SEQ ID NO:35 ERCLQYLVQY |
| γ2T (γ2 V->T) | SEQ ID NO:22 CLQYLTC |

Figure 4:
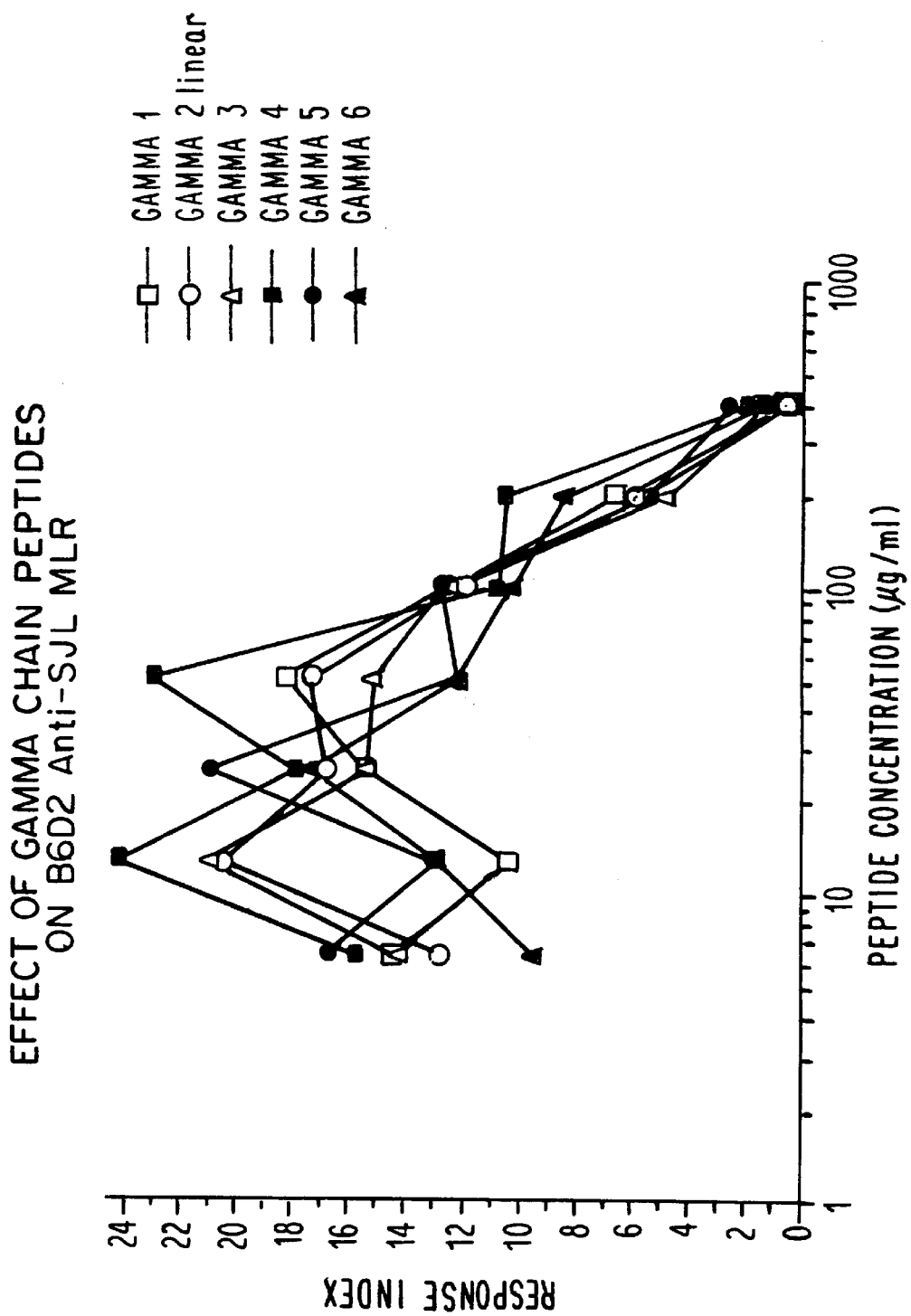
FIG. 4 shows data from experiments described in Example 1 testing the ability of peptides of the invention as described in Example 1 to inhibit mixed lymphocyte responses (MLR assays as described in Example 2).
Figure 6A:
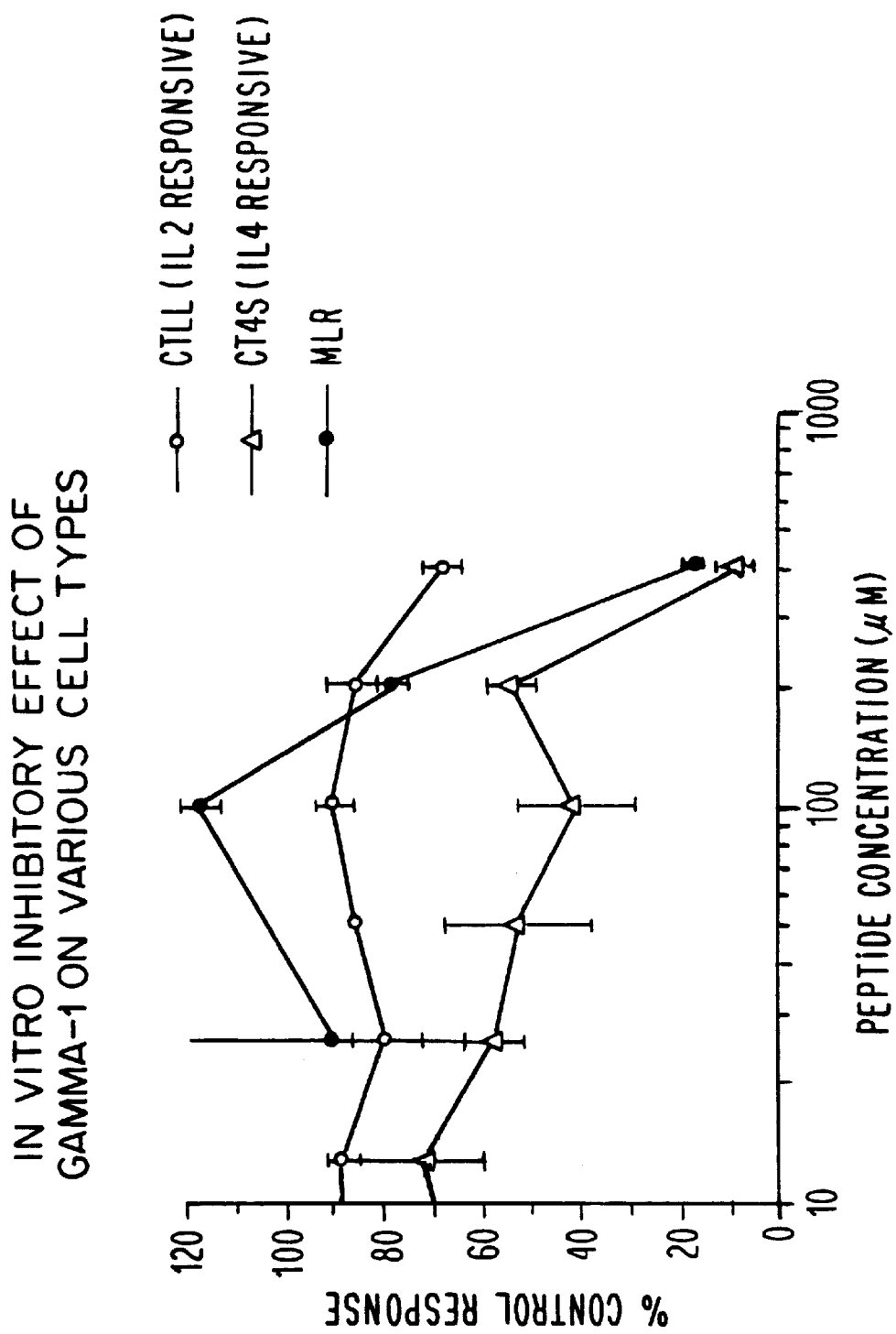
Figure 6B:
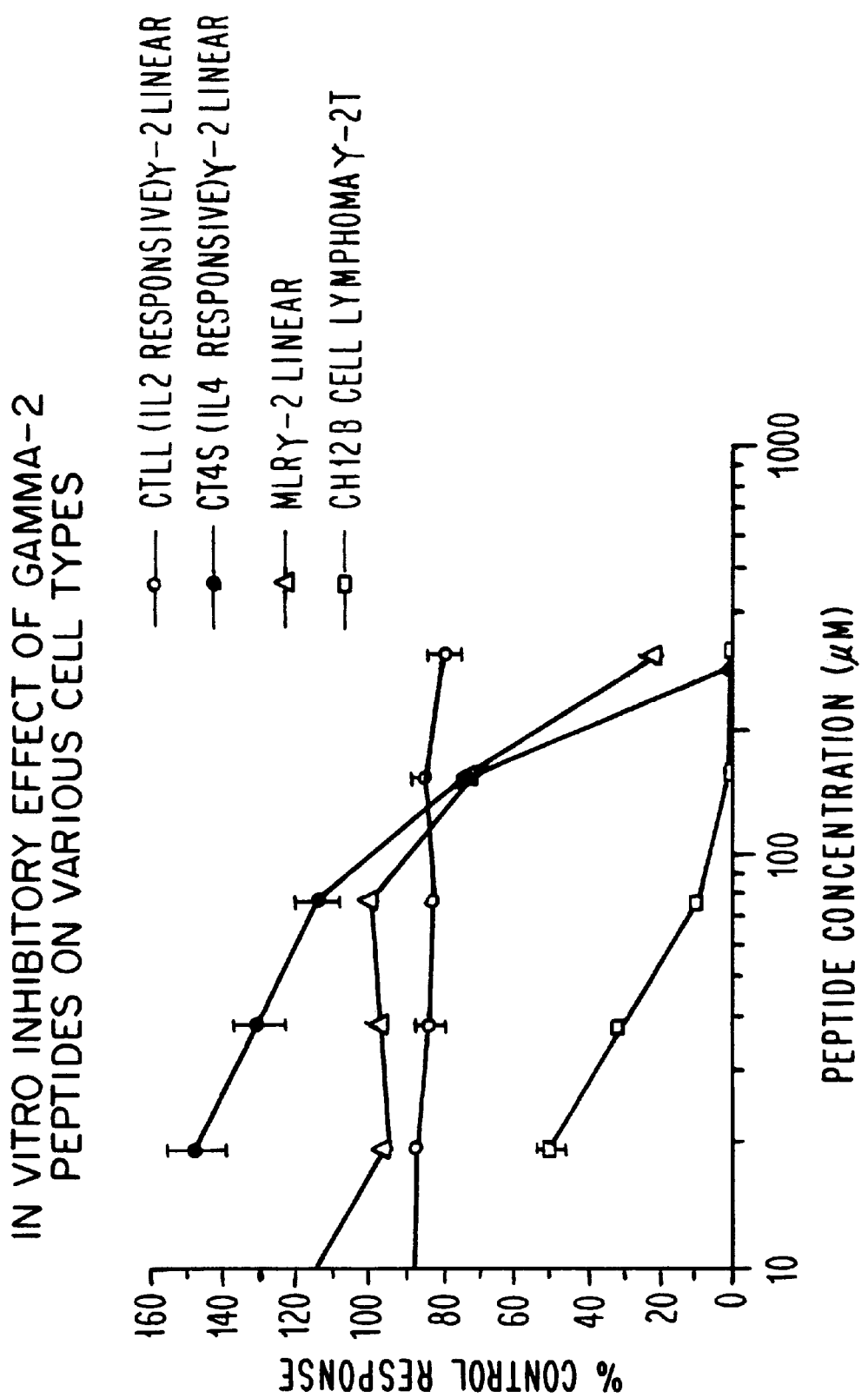
Figure 6C:
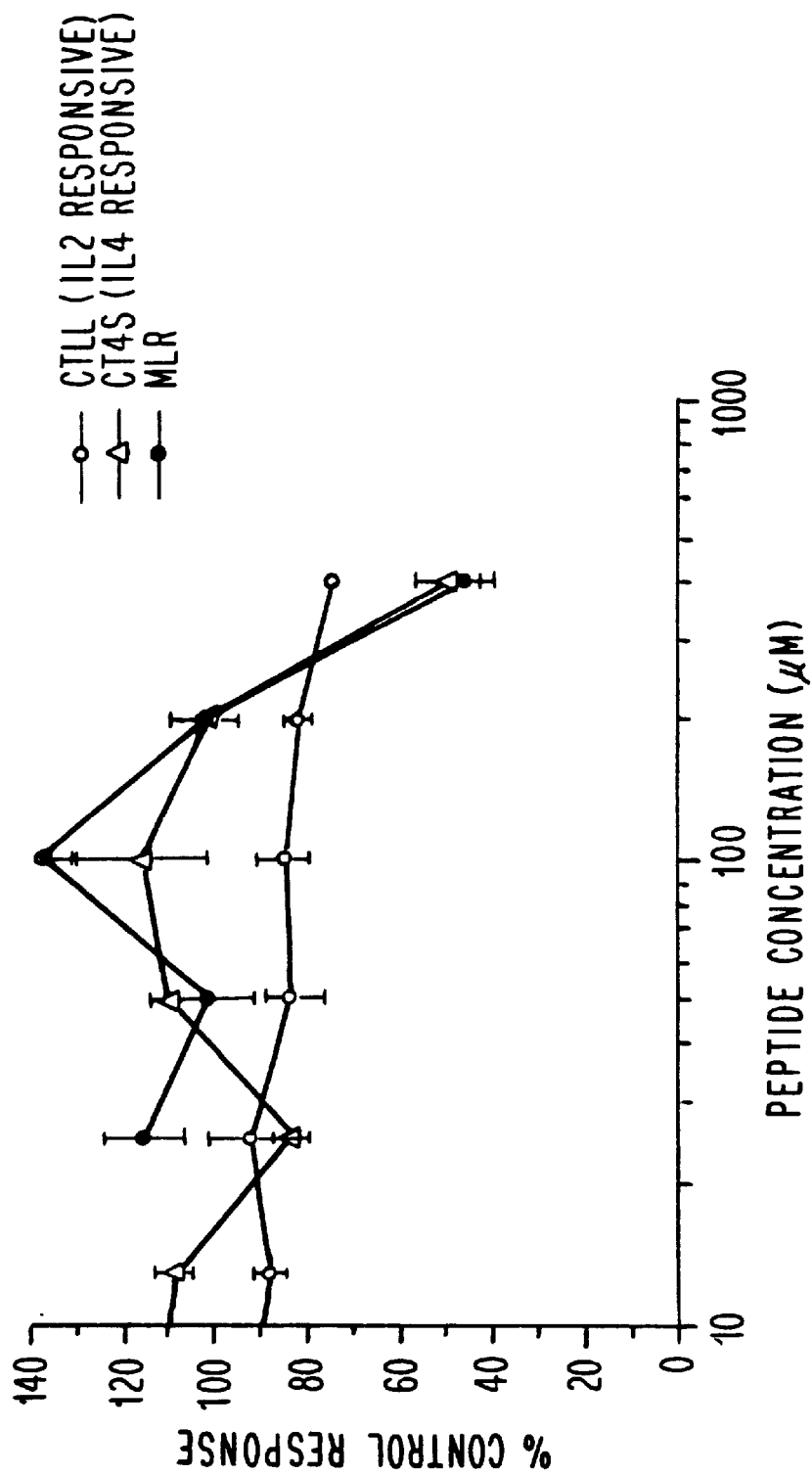
Figure 6E:
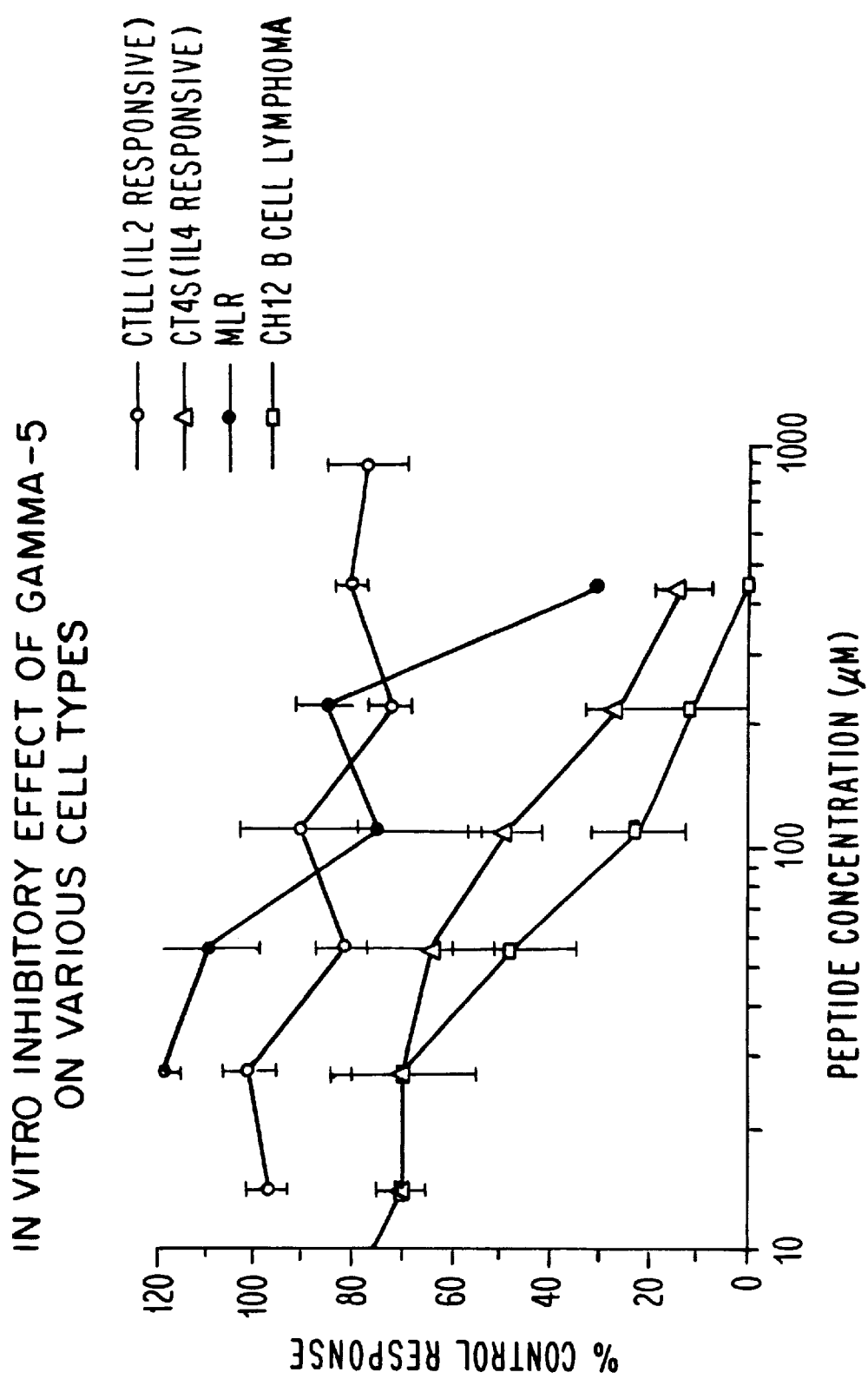
Figure 6F:
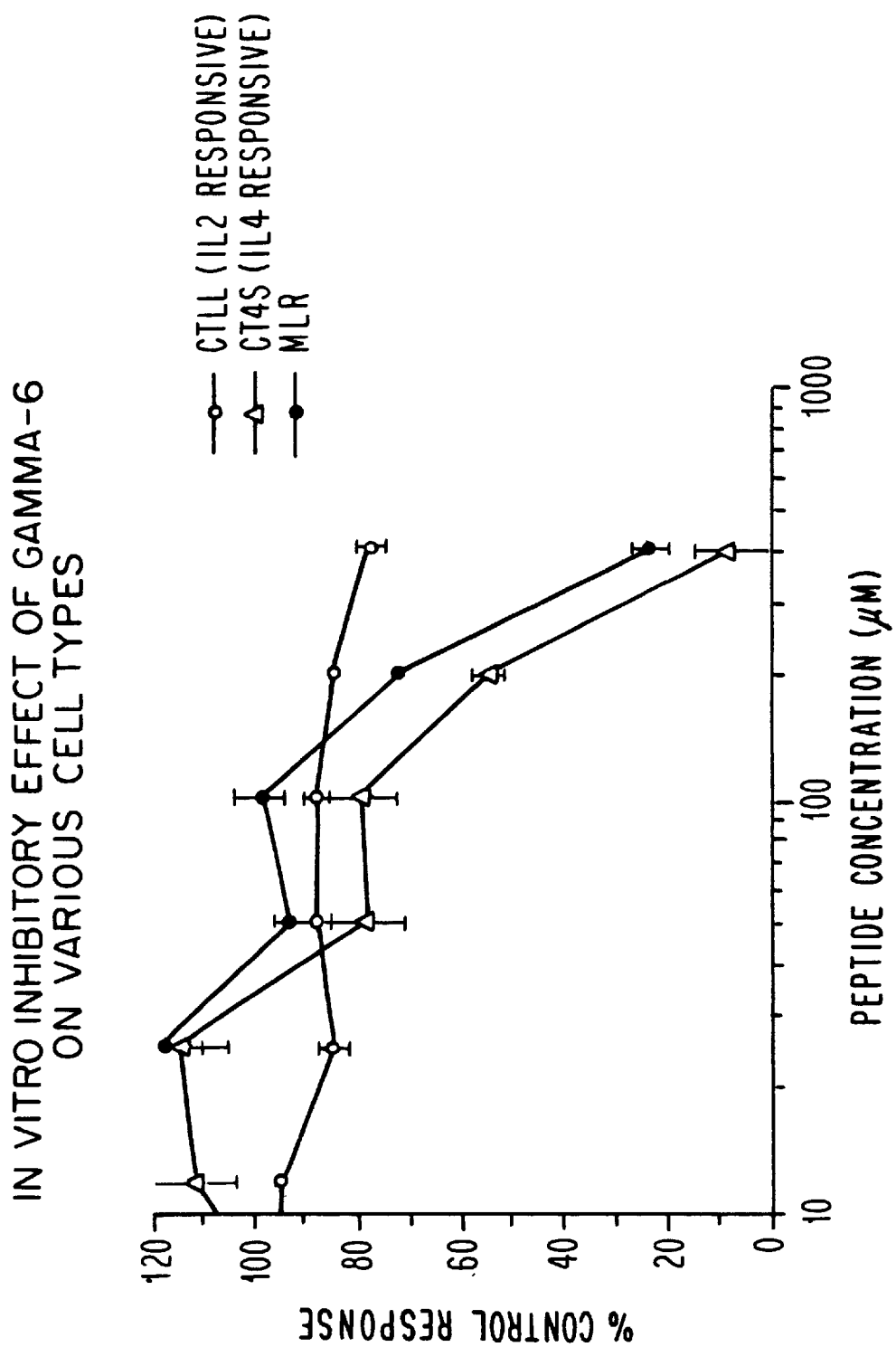

The murine sequences have been tested in at least two of these proliferation assays. FIGS. 1A–1D, 2 and 3 show the ability of these peptides to inhibit IL-4 induced proliferation of CTLL's. FIG. 4 shows the ability of these peptides to inhibit MLRs and FIG. 5 shows the ability of these peptides to inhibit CH12.CX proliferation.

These data suggest that these peptides can in fact inhibit cytokine responses in vitro. These peptides do not appear to be toxic as the CTLL proliferation to IL-2 is not affected.

Example 2

Experiments were performed to test the effect of each of peptides gamma-1, gamma-2, gamma-3, gamma-4, gamma-5 and gamma-6 on different cell types using several different assays. The data from the experiments is shown in FIGS. 6A–6F. The assays were performed as follows:

CTLL Proliferation Assay: The murine IL-2- and IL-4-responsive CTLL cell line was used to assess the ability of the gamma chain peptides to inhibit the binding of these cytokines to their respective receptors. The cell line proliferates in responses to exogenously added cytokine and inhibition of this proliferation by the peptides would be a result of blocking the cytokines from interacting with their receptors. Briefly, 5000 CTLL cells are added to the wells of a 96 well microtitre plate. Either 10 U/ml r-mIL-2 or 1 ng/ml r-mIL-4 are added to these wells along with titred amounts of the indicated peptides. Cultures are incubated at 37° C. for 24 hours and pulsed with $^3$H-TdR for the final 6 hours to indicate amount of proliferation. Wells containing no peptide are deemed the positive response and well containing no peptide and no cytokine are deemed the background (bkg) proliferation. A percent response is calculated as follows: (CPM experimental-CPM bkg)/CPM positive response-CPM bkg). All data are expressed in this manner.

CT4S Proliferation Assay: The murine IL-4 responsive CT4S cell line was used to assess the ability of the gamma chain peptides to inhibit the binding of IL-4 to its receptor. The cell line proliferates in responses to exogenously added mIL-4 and inhibition of this proliferation by the peptides would be a result of blocking the mIL-4 from interacting with their receptors. Briefly, 5000 CT4S cells are added to the wells of a 96 well microtitre plate. r-mIL-4 (50 pg/ml) is added to these wells along with titred amounts of the indicated peptides. Cultures are incubated at 37° C. for 48 hours and pulsed with $^3$H-TdR for the final 6 hours to indicate amount of proliferation. Wells containing no peptide are deemed the positive response and wells containing no peptide and no cytokine are deemed the background (bkg) proliferation. A percent response is calculated as follows: (CPM experimental-CPM bkg)/(CPM positive response-CPM bkg). All data are expressed in this manner.

CH12 Proliferation Assay: The CH12 murine B cell lymphoma, like many lymphomas, is an IL-4 producing cell line that is also dependent on IL-4 for proliferation. No exogenous IL-4 is added to the wells of these cultures. Briefly, 1500 cells are added to each well along with titred amounts of the indicated peptides. Cultures are incubated at 37° C. for 48 hours and pulsed with $^3$H-TdR for the final 6 hours to indicate amount of proliferation. Wells containing no peptide are deemed the positive response and there is no true background response. A percent response is calculated as follows: (CPM experimental)/(CPM positive response). All data are expressed in this manner.

Mixed Lymphocyte Assay: Allogeneic murine mixed lymphocyte response assays were performed to determine if the gamma chain peptides were capable of inhibiting this response as well. Assays were performed as previously described. Briefly, responder lymph node cells were isolated from SJL mice and stimulator spleen cells were located from (B6×CBA) $F_1$ mice responder cells ($2\times10^5$/well) were plated in 96 well plates along with irradiated stimulator cells ($4\times10^5$/well). Titred amounts of gamma chain peptides were added to the indicated wells. Cultures are incubated at 37° C. for 3 days and pulsed with $^3$H-TdR for the final 18 hours to indicate amount of proliferation. Wells containing no peptide and both stimulator and responder cells are deemed the positive response and wells containing no peptide and no stimulator cells are deemed the background (bkg) proliferation. A percent response is calculated as follows: (CPM experimental-CPM bkg)/(CPM positive response-CPM bkg). All data are expressed in this manner.

In vitro testing using human cells and in vivo testing was performed as follows.

Figure 7:
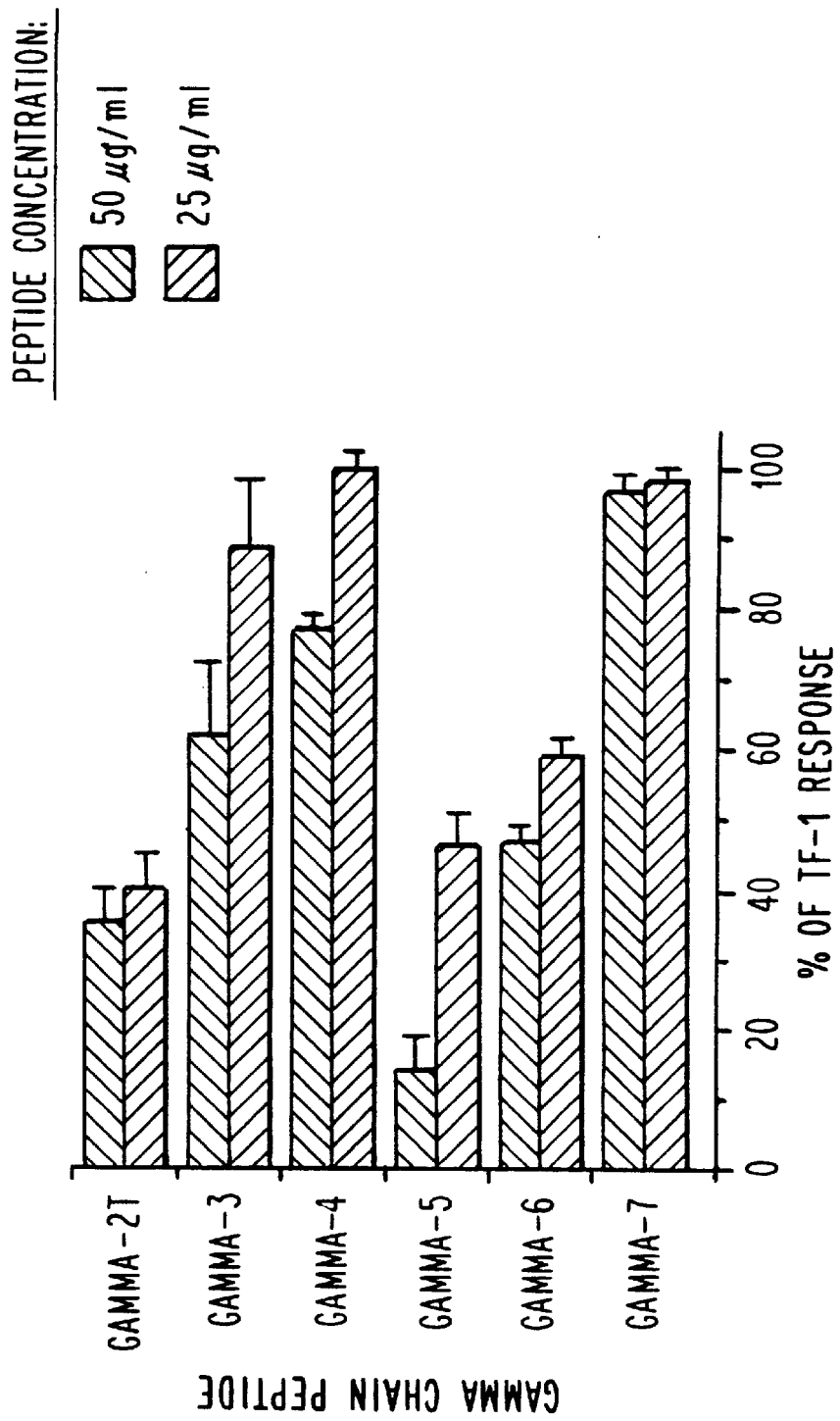
FIG. 7 shows data from experiments described in Example 2 testing the ability of peptides of the invention as described in Example 1 to inhibit human IL-4 mediated activity.

TF-1 Proliferation Assay: The TF-1 cell line is a human cell line that is responsive to several cytokine including human IL-4. Inhibition of IL-4 induced proliferation of this cell indicates that these peptides are capable if inhibiting human IL-4. Briefly, TF-1 cells are rested (Cultured in the absence of cytokines) for 48 hours prior to the initiation of the assay. Cells are plated (20000/well) along with titred amounts of the indicated peptides and 1 ng/ml r-hIL-4). Cultures are incubated at 37° C. for 48 hours and pulsed with $^3$H-TdR for the final 6 hours to indicate amount of proliferation. Wells containing no peptide are deemed the positive response and wells containing no peptide and no cytokine are deemed the background (bkg) proliferation. A percent response is calculated as follows: (CPM experimental-CPM bkg)/(CPM positive response-CPM bkg). All data are expressed in this manner. The results are shown in FIG. 7.

Figure 8:
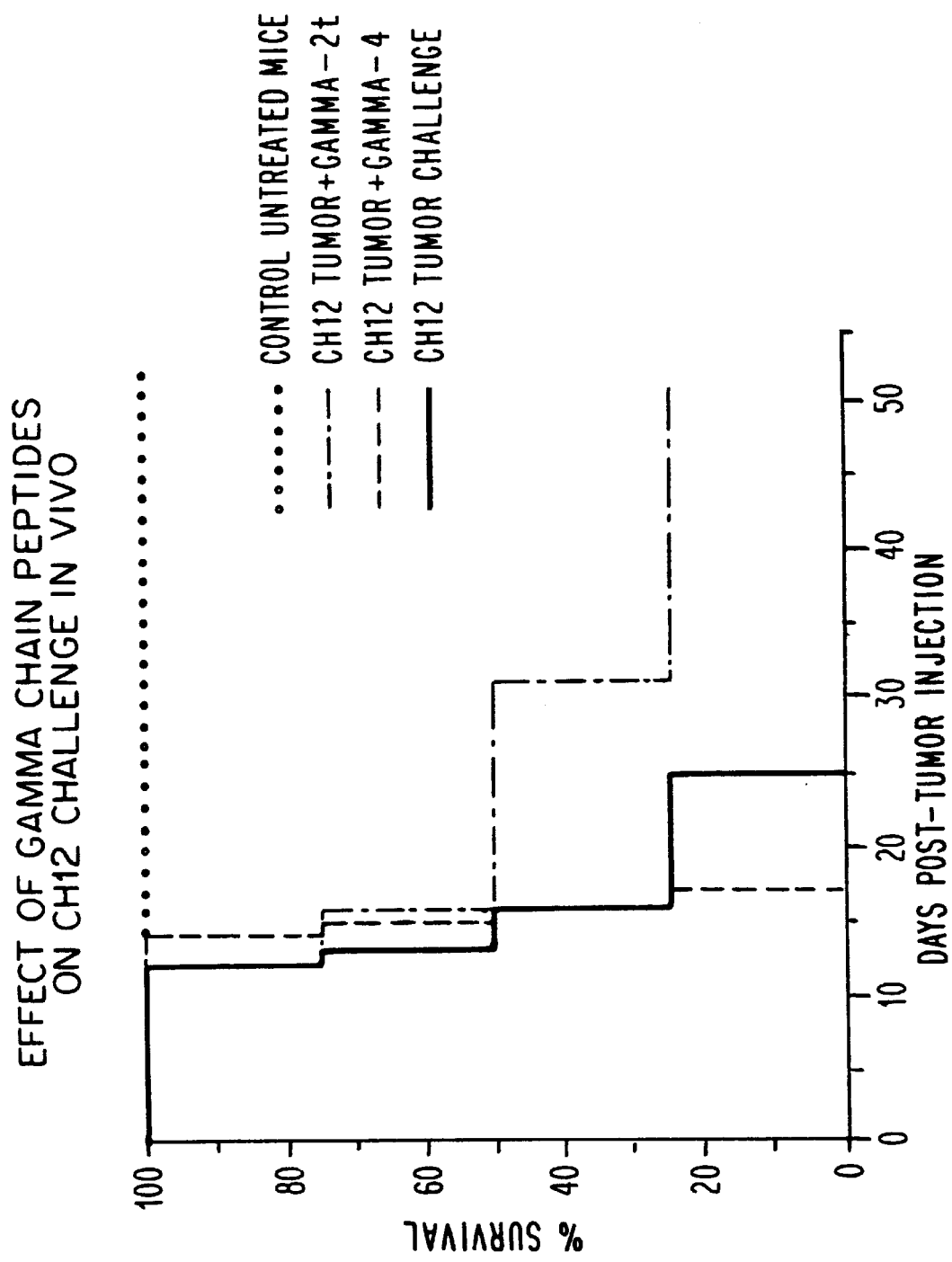
FIG. 8 shows data from experiments described in Example 2 testing the ability of peptides of the invention as described in Example 1 to inhibit cytokine mediated activity of cells in vivo.

Effect of Gamma Chain Peptides In Vivo: In order to evaluate the efficacy of these peptides in vivo, we challenged sub-lethally (500 Rads) irradiated B10.A mice with $2 \times 10^5$ CH12 (B-cell Lymphoma) cells and tracked the lethal effects of this tumor challenge. Indicated groups of mice (4/group) received either no treatment, gamma 2T (0.5 mg i.p. on days 0,3,6), of gamma4 (0.5 mg i.p. on days 0,3,6). Data is represented as % survival. The data is shown on FIG. 8.

What is claimed is:

1. A peptide wherein said peptide mimics a loop on the γ-chain that interacts with either a cytokine or a γ-chain partner receptor chain of a heterodimeric cytokine receptor, consists of 5–25 amino acids, inhibits signal transduction mediated by cytokine:receptor binding of cytokines that bind to receptors that comprise a γ-chain, is conformationally restricted, and is selected from the group consisting of: SEQ ID NO:18 CIQLYQTFC; SEQ ID NO:19 CIHLYQTFC; SEQ ID NO:20 CLQYLVC; SEQ ID NO:21 CLEHLVC; SEQ ID NO:22 CLQYLTC; SEQ ID NO:23 CLEHTC; SEQ ID NO:24 CLQYLTQC; SEQ ID NO:25 CLEHLTQC; SEQ ID NO:26 CPIAGSSQQC; SEQ ID NO:37 CPICGSSQQC; SEQ ID NO:27 CPLCGSAQHC; SEQ ID NO:28 CPLAGSAQHC; SEQ ID NO:29 CNHEPRFLSC; SEQ ID NO:30 CDYRHKFSLC; SEQ ID NO:31 CLNLQNLC; SEQ ID NO:32 CLKLQNLC; SEQ ID NO:33 CNLSESQLC; and SEQ ID NO:34 CKLSESQLC.

2. A peptide wherein said peptide mimics a loop on the γ-chain that interacts with either a cytokine or a γ-chain partner receptor chain of a heterodimeric cytokine receptor consists of 5–25 amino acids, inhibits signal transduction mediated by cytokine:receptor binding of cytokines that bind to receptors that comprise a γ-chain, is conformationally restricted, is cyclic and is selected from the group consisting of: SEQ ID NO:18 CIQLYQTFC; SEQ ID NO:19 CIHLYQTFC; SEQ ID NO:20 CLQYLVC; SEQ ID NO:21 CLEHLVC; SEQ ID NO:22 CLQYLTC; SEQ ID NO:23 CLEHLTC; SEQ ID NO:24 CLQYLTQC; SEQ ID NO:25 CLEHLTQC; SEQ ID NO:26 CPIAGSSQQC; SEQ ID NO:37 CPICGSSQQC; SEQ ID NO:27 CPLCGSAQHC; SEQ ID NO:28 CPLAGSAQHC; SEQ ID NO:29 CNHEPRFLSC; SEQ ID NO:30 CDYRHKFSLC; SEQ ID NO:31 CLNLQNLC; SEQ ID NO:32 CLKLQNLC; SEQ ID NO:33 CNLSESQLC and SEQ ID NO:34 CKLSESQLC.

3. A peptide wherein said peptide mimics a loop on the γ-chain that interacts with either a cytokine or a γ-chain partner receptor chain of a heterodimeric cytokine receptor, consists of 5–25 amino acids, inhibits signal transduction mediated by cytokine:receptor binding of cytokines that bind to receptors that comprise a γ-chain, and is a conformationally restricted peptide having the formula:

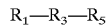

$$R_1 - R_3 - R_5$$

wherein:

R$_1$ is a linking moiety;

R$_3$ is SEQ ID NO: 1 IQLYQTF; SEQ ID NO:2 IHLYQTF; SEQ ID NO:3 CLQYLV; SEQ ID NO:4 CLEHLV; SEQ ID NO:5 CLQYLT; SEQ ID NO:6 CLEHLT; SEQ ID NO:7 CLQYLTQ; SEQ ID NO:8 CLEHLTQ; SEQ ID NO:9 PIAGSSQQ; SEQ ID NO:36 PICGSSQQ; SEQ ID NO:10 PLCGSAQH; SEQ ID NO:11 PLAGSAQH; SEQ ID NO:12 NHEPRFLS; SEQ ID NO:13 DYRHKFSL; SEQ ID NO:14 LNLQNL; SEQ ID NO:15 LKLQNL; SEQ ID NO:16 NLSESQL; or SEQ ID NO:17 KLSEQL; and R$_5$ is a linking moiety.

4. The peptide of claim 3 wherein:

R$_3$ is SEQ ID NO:14 LNLQNL.

5. A pharmaceutical composition comprising a peptide of claim 1 and a pharmaceutically acceptable carrier or diluent.

6. The pharmaceutical composition of claim 5 wherein said peptide is cyclic.

7. The pharmaceutical composition of claim 5 wherein said peptide is SEQ ID NO:31 CLNLQNLC.

8. A pharmaceutical composition comprising a peptide and a pharmaceutically acceptable carrier or diluent, wherein said peptide mimics a loop on the γ-chain that interacts with either a cytokine or a γ-chain partner receptor chain of a heterodimeric cytokine receptor consists of 5–25 amino acids, inhibits signal transduction mediated by cytokine:receptor binding of cytokines that bind to receptors that comprise a γ-chain, is a conformationally restricted peptide having the formula:

$$R_1—R_3—R_5$$

wherein:

$R_1$ is a linking moiety;

$R_3$ is SEQ ID NO:1 IQLYQTF; SEQ ID NO:2 IHLYQTF; SEQ ID NO:3 CLQYLV; SEQ ID NO:4 CLEHLV; SEQ ID NO:5 CLQYLT; SEQ ID NO:6 CLEHLT; SEQ ID NO:7 CLQYLTQ; SEQ ID NO:8 CLEHLTQ; SEQ ID NO:9 PIAGSSQQ; SEQ ID NO:36 PICGSSQQ; SEQ ID NO:10 PLCGSAQH; SEQ ID NO:11 PLAGSAQH; SEQ ID NO:12 NHEPRFLS; SEQ ID NO:13 DYRHKFSL; SEQ ID NO:14 LNLQNL; SEQ ID NO:15 LKLQNL; SEQ ID NO:16 NLSESQL; SEQ ID NO:17 KLSEQL; and $R_5$ is a linking moiety.

9. The pharmaceutical composition of claim 8 wherein:

$R_3$ is SEQ ID NO:14 LNLQNL.

10. The peptide of claim 1 wherein said peptide is: SEQ ID NO:31 CLNLQNLC.

* * * * *

UNITED STATES PATENT AND TRADEMARK OFFICE
CERTIFICATE OF CORRECTION

PATENT NO. : 6,346,602 B1
DATED : February 12, 2002
INVENTOR(S) : Townsend et al.

It is certified that error appears in the above-identified patent and that said Letters Patent is hereby corrected as shown below:

Title page, Item [54] and Column 1, line 2,
Please delete "γ" and insert therefor -- GAMMA --;

Column 9,
Line 40, (1st Table), please delete "[001b]";

Signed and Sealed this

Seventeenth Day of September, 2002

Attest:

Attesting Officer

JAMES E. ROGAN
*Director of the United States Patent and Trademark Office*